(12) United States Patent
Keenan et al.

(10) Patent No.: US 9,289,168 B2
(45) Date of Patent: Mar. 22, 2016

(54) SYSTEM AND/OR METHOD FOR GLUCOSE SENSOR CALIBRATION

(75) Inventors: Desmond Barry Keenan, Los Angeles, CA (US); John J. Mastrototaro, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1379 days.

(21) Appl. No.: 12/345,477

(22) Filed: Dec. 29, 2008

(65) Prior Publication Data

US 2010/0162786 A1 Jul. 1, 2010

(51) Int. Cl.
| | |
|---|---|
| G01N 33/48 | (2006.01) |
| G01N 31/00 | (2006.01) |
| G06G 7/48 | (2006.01) |
| G06G 7/58 | (2006.01) |
| A61B 5/1495 | (2006.01) |
| A61B 5/145 | (2006.01) |
| A61B 5/00 | (2006.01) |

(52) U.S. Cl.
CPC ........... *A61B 5/1495* (2013.01); *A61B 5/14532* (2013.01); *A61B 5/6849* (2013.01)

(58) Field of Classification Search
CPC .......... G01N 2500/00; G01N 33/6893; G01N 2800/52; A61B 2560/0223; A61B 8/58
See application file for complete search history.

(56) References Cited

U.S. PATENT DOCUMENTS

| | | |
|---|---|---|
| 4,562,751 A | 1/1986 | Nason |
| 4,573,994 A | 3/1986 | Fischell |
| 4,678,408 A | 7/1987 | Nason |
| 4,685,903 A | 8/1987 | Cable |
| 5,299,571 A | 4/1994 | Mastrototaro |
| 5,390,671 A | 2/1995 | Lord |
| 5,391,250 A | 2/1995 | Cheney, II |
| 5,399,571 A | 3/1995 | Yamamoto et al. |
| 5,482,473 A | 1/1996 | Lord |
| 5,586,553 A | 12/1996 | Halili |
| 5,951,521 A | 9/1999 | Mastrototaro |
| 5,954,643 A | 9/1999 | VanAntwerp |
| 6,360,888 B1 | 3/2002 | McIvor |
| 6,368,141 B1 | 4/2002 | VanAntwerp |
| 6,641,533 B2 | 11/2003 | Causey, III |
| 6,895,263 B2 | 5/2005 | Shin et al. |
| 7,029,444 B2 * | 4/2006 | Shin et al. ..................... 600/365 |
| 7,324,012 B2 | 1/2008 | Mann |
| 7,389,133 B1 * | 6/2008 | Kotulla et al. ................. 600/345 |
| 7,405,055 B2 * | 7/2008 | Dunn et al. ..................... 435/14 |

(Continued)

FOREIGN PATENT DOCUMENTS

WO WO98/21246 5/1998

OTHER PUBLICATIONS

U.S. Appl. No. 60/121,656, filed Feb. 25, 1999, 25 pages.

(Continued)

*Primary Examiner* — Larry D Riggs, II
(74) *Attorney, Agent, or Firm* — Berkeley Law & Technology Group LLP

(57) ABSTRACT

The subject matter disclosed herein relates to systems, methods and/or devices for calibrating sensor data to be used in estimating a blood glucose concentration. A relationship between sensor measurements and reference readings may be used to estimate a relationship between sensor measurements and blood glucose concentration. Such sensor measurements may be weighted according to a decreasing function of uncertainty associated with sensor values.

30 Claims, 17 Drawing Sheets

(56) References Cited

U.S. PATENT DOCUMENTS

2002/0161288 A1  10/2002  Shin et al.
2008/0312845 A1  12/2008  Hayter et al.

OTHER PUBLICATIONS

U.S. Appl. No. 60/121,664, filed Feb. 25, 1999, 22 pages.
U.S. Appl. No. 60/121,655, filed Feb. 25, 1999, 33 pages.
PCT/US2009/006677: PCT application as filed on Dec. 22, 2009, 55 pages.
PCT/US2009/006677: Initial Publication with International Search Report on Jul. 8, 2010, 57 pages.
PCT/US2009/006677: International Search Report mailed Mar. 29, 2010, 3 pages.
PCT/US2009/006677: Written Opinion of the International Search Authority, mailed Jun. 29, 2011, 5 pages.
PCT/US2009/006677: International Preliminary Report on Patentability mailed Jun. 29, 2011, 6 pages.
EP09801592.9: amended claims filed with nationalized EP application, filed Jun. 8, 2011, 8 pages.
EP09801592.9: EPO communication regarding written opinion/amendment mailed Aug. 5, 2011, 2 pages.

* cited by examiner

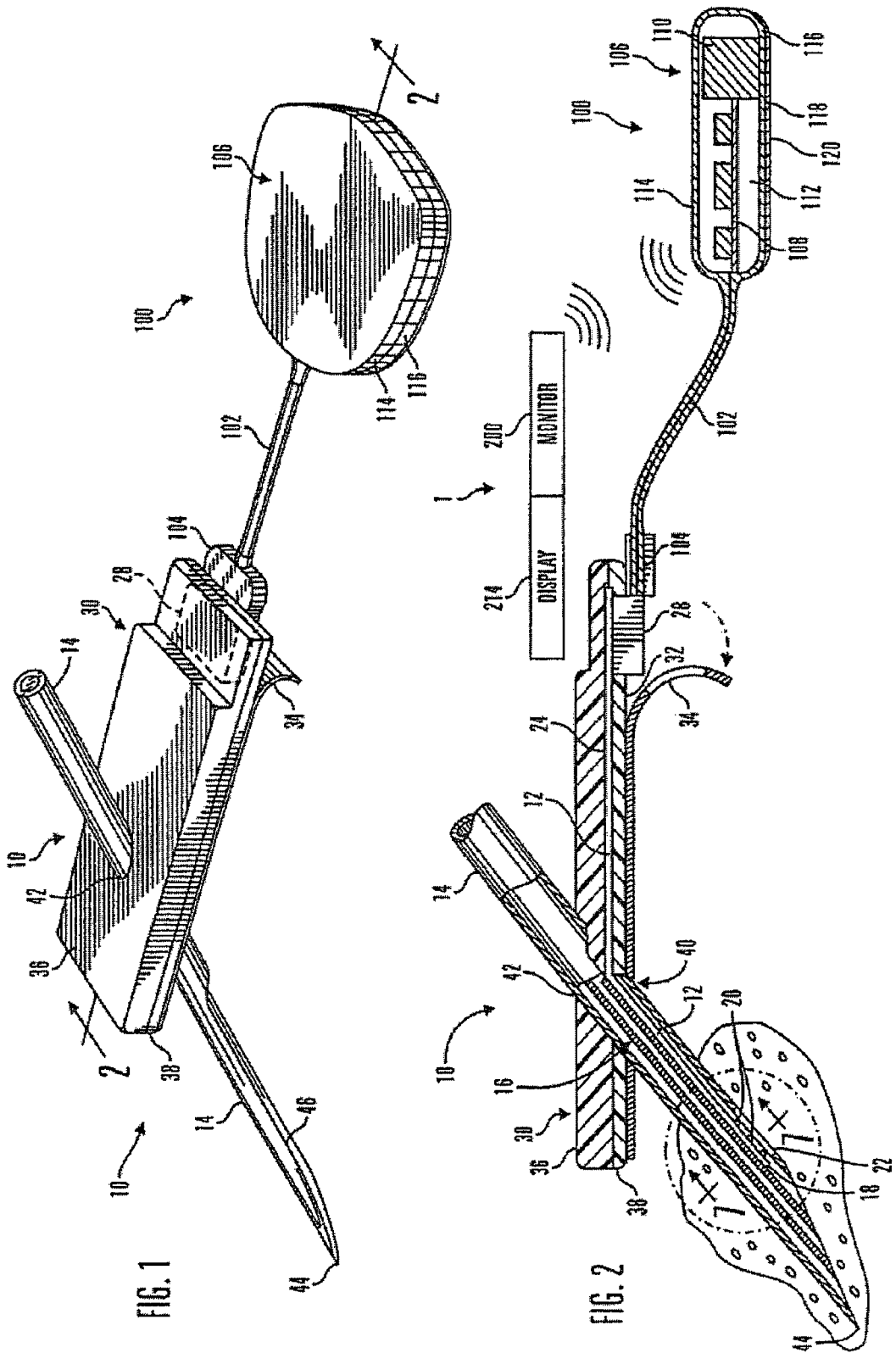

FIG. 10

| | A | B | C | D | E | F | G | H | I | J | K | L | M | N | O | P |
|---|---|---|---|---|---|---|---|---|---|---|---|---|---|---|---|---|
| 1 | PATIENT ID | SAMPLE | DATE | TIME | ISIG VALUE | VCTR | METER VALUE | SLOPE | OFFSET | VALID ISIG | SENSOR ISIG VALUE | POWER UP | POWER DOWN | SENSOR INITIALIZATION | LINK EVENT | SENSOR DISCONNECT |
| 2 | 000-0000 | 0 | 7/10/98 | 10:53 | 0 | -2.042 | | | | | | | | | | |
| 3 | 000-0000 | 1 | 7/10/98 | 10:58 | 0 | -2.026 | | | | | | | | | | SED |
| 4 | 000-0000 | 2 | 7/10/98 | 11:03 | 0 | -1.732 | | | | | | | | | | |
| 5 | 000-0000 | 3 | 7/10/98 | 11:09 | 99.1 | -0.936 | | | | | | | | | | |
| 6 | 000-0000 | 4 | 7/10/98 | 11:14 | 19.7 | -0.565 | | | | | | | | | | |
| 7 | 000-0000 | 5 | 7/10/98 | 11:19 | 26.1 | -0.598 | | | | | | | | | | |
| 8 | 000-0000 | 6 | 7/10/98 | 11:24 | 25.7 | -0.626 | | | | | | | | | | |
| 9 | 000-0000 | 7 | 7/10/98 | 11:29 | 26 | -0.643 | | | | | | | | | | |
| 10 | 000-0000 | 8 | 7/10/98 | 11:34 | 24.9 | -0.648 | | | | | | | | | | |
| 11 | 000-0000 | 9 | 7/10/98 | 11:39 | 23.9 | -0.649 | | | | | | | | | | |
| 12 | 000-0000 | 10 | 7/10/98 | 11:44 | 23.8 | -0.651 | | | | | | | | | | |
| 13 | 000-0000 | 11 | 7/10/98 | 11:49 | 24.3 | -0.658 | | | | | | | | | | |
| 14 | 000-0000 | 12 | 7/10/98 | 11:54 | 23.9 | -0.655 | | | | | | | | | | |
| 15 | 000-0000 | 13 | 7/10/98 | 11:59 | 23 | -0.652 | | | | | | | | | | |
| 16 | 000-0000 | 14 | 7/10/98 | 12:04 | 23.3 | -0.652 | | | | | | | | | | |
| 17 | 000-0000 | 15 | 7/10/98 | 12:09 | 22.2 | -0.645 | | | | | | | | | | |
| 18 | 000-0000 | 16 | 7/10/98 | 12:14 | 22.1 | -0.644 | 95 | 5.0 | 3 | 22.1 | 96 | | | | | |
| 19 | 000-0000 | 17 | 7/10/98 | 12:19 | 20.1 | -0.634 | | | | 20.1 | 80 | | | | | |
| 20 | 000-0000 | 18 | 7/10/98 | 12:24 | 19.9 | -0.637 | | | | 19.9 | 85 | | | | | |
| 21 | 000-0000 | 19 | 7/10/98 | 12:29 | 20.6 | -0.645 | | | | 20.6 | 88 | | | | | |
| 22 | 000-0000 | 20 | 7/10/98 | 12:34 | 20.8 | -0.662 | | | | 20.8 | 89 | | | | | |
| 23 | 000-0000 | 21 | 7/10/98 | 12:39 | 19.1 | -0.645 | | | | 19.1 | 81 | | | | ESI | |
| 24 | 000-0000 | 22 | 7/10/98 | 12:44 | 18.2 | -0.635 | | | | 18.2 | 76 | | | | | |
| 25 | 000-0000 | 23 | 7/10/98 | 12:49 | 17.4 | -0.633 | | | | 17.4 | 72 | | | | | |
| 26 | 000-0000 | 24 | 7/10/98 | 12:54 | 16.4 | -0.625 | | | | 16.4 | 67 | | | | | |
| 27 | 000-0000 | 25 | 7/10/98 | 12:59 | 15.7 | -0.619 | | | | 15.7 | 64 | | | | | |
| 28 | 000-0000 | 26 | 7/10/98 | 13:04 | 15 | -0.612 | | | | 15 | 60 | | | | | |
| 29 | 000-0000 | 27 | 7/10/98 | 13:09 | 13.8 | -0.602 | | | | 13.8 | 54 | | | | | |
| 30 | 000-0000 | 28 | 7/10/98 | 13:14 | 13.3 | -0.597 | | | | 13.3 | 52 | | | | | |
| 31 | 000-0000 | 29 | 7/10/98 | 13:19 | 14.4 | -0.62 | | | | 14.4 | 57 | | | | | |
| 32 | 000-0000 | 30 | 7/10/98 | 13:24 | 16 | -0.635 | | | | 16 | 65 | | | | | |

SYSTEM AND/OR METHOD FOR GLUCOSE SENSOR CALIBRATION

BACKGROUND

1. Field

The subject matter disclosed herein relates to calibration of glucose sensors for use in glucose monitoring systems, for example.

2. Information

Over the years, body characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in a body characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors are being developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994. Typical thin film sensors are described in commonly assigned U.S. Pat. Nos. 5,390,671; 5,391,250; 5,482,473; and 5,586,553. See also U.S. Pat. No. 5,299,571.

SUMMARY

Briefly, one embodiment relates to a method, system and/or apparatus for obtaining samples of an electrical signal generated by a sensor, said samples having sample values associated with measurements of a blood-glucose concentration; individually weighting at least some of said sample values according to a function of blood glucose reference samples associated with said sample values; and estimating a relationship of sample values with said blood-glucose concentration based, at least in part, on said individually weighted samples.

In another implementation estimating said relationship comprises estimating a linear relationship between said sample values and said blood-glucose concentration based, at least in part, on a linear regression of said weighted samples and associated blood-glucose reference values. Here, for example, such estimating said linear relationship may further comprise calculating a linear regression sensitivity ratio based, at least in part, on said weighted samples and associated blood-glucose reference values; selecting an offset based, at least in part, on said calculated linear regression sensitivity ratio; and calculating a modified linear regression sensitivity ratio based, at least in part, on said selected offset, said weighted samples and said associated blood-glucose reference values.

In another particular implementation the function of blood glucose reference samples is based, at least in part, on a measure of statistical dispersion of said sample values as function of associated blood glucose reference samples. Here, for example, said measure of statistical dispersion may comprise a variance and/or approximation of a variance of said sample values as a function of said associated blood glucose reference samples. Alternatively, the function may comprise an inverse of said measure of statistical dispersion of said sample values. In yet another alternative, the method includes estimating a linear relationship of said measure of statistical dispersion of said sample values versus blood glucose concentration; and deriving the function based, at least in part, on said linear relationship.

In another particular implementation, individually weighting said at least some of said sample values further comprises further weighting said samples based on how recently said samples are obtained.

In another particular implementation, the method includes detecting a failure of said sensor based, at least in part, on a change in said estimated relationship.

In another particular implementation, the method includes calibrating measurements from said sensor for measuring a blood-glucose concentration based, at least in part, on said estimated relationship.

In another particular implementation, individually weighting said at least some of said sample values comprises weighting said at least some of said sample values according to a decreasing function of blood glucose reference values associated with said weighted samples.

Particular embodiments may be directed to an article comprising a storage medium including machine-readable instructions stored thereon which, if executed by a computing platform, are directed to enable the computing platform to execute at least a portion of the aforementioned method according to one or more of the particular aforementioned implementations. In other particular embodiments, a sensor adapted generate one or more signals responsive to a blood glucose concentration in a body while a computing platform is adapted to perform the aforementioned method according to one or more of the particular aforementioned implementations based upon the one or more signals generated by the sensor.

BRIEF DESCRIPTION OF THE FIGURES

Non-limiting and non-exhaustive features will be described with reference to the following figures, wherein like reference numerals refer to like parts throughout the various figures.

FIG. 1 is a is a perspective view illustrating a subcutaneous glucose sensor insertion set and glucose monitor device in accordance with an embodiment;

FIG. 2 is a cross-sectional view of the sensor set and glucose monitor device as shown along the line 2-2 of FIG. 1;

FIG. 10 is a sample computer screen shot image of a post processor analysis of glucose monitor data according to an embodiment;

DETAILED DESCRIPTION

Figure 3:
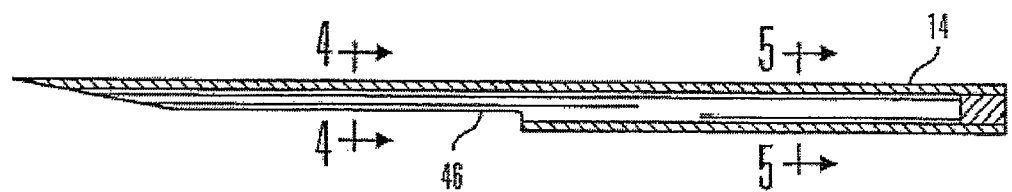
FIG. 3 is a cross-sectional view of a slotted insertion needle used in the insertion set of FIGS. 1 and 2.
Figure 4:
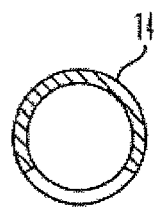
FIG. 4 is a cross-sectional view as shown along line 4-4 of FIG. 3.
Figure 5:
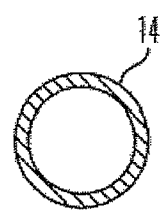
FIG. 5 is a cross-sectional view as shown along line 5-5 of FIG. 3.
Figure 6:
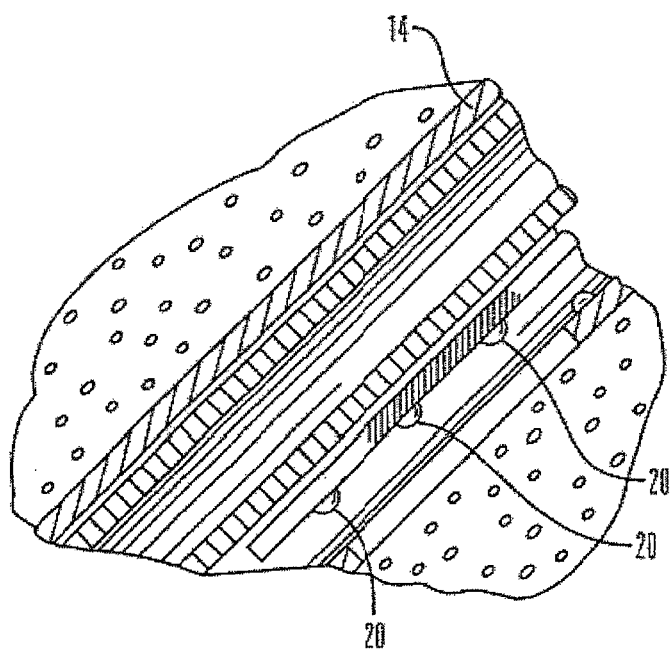
FIG. 6 is a partial cross-sectional view corresponding generally with the encircled region 6 of FIG. 2.
Figure 7:
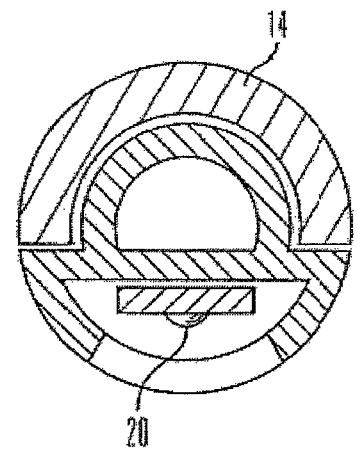
FIG. 7 is a cross-sectional view as shown along line 7-7 of FIG. 2.

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

Systems for monitoring glucose in the body, for the treatment of diabetes for example, typically employ one or more glucose sensors to measure a blood-glucose concentration. For example, such sensors may be adapted to generate one or more electrical signals having a value (e.g., voltage and/or current level) that is related to such a blood-glucose concentration. Such a measurement of a blood-glucose concentration may then be used for any one of several applications such as, for example, monitoring a blood-glucose concentration for a diabetes patient.

Over time and/or with normal wear and usage of a glucose sensor, such a relationship between a value of a signal generated by the glucose monitoring blood sensor and actual measured blood glucose concentration may change. Accordingly, calibration of the signal generated by such a glucose monitoring with reference samples of blood-glucose concentration may enable an accurate estimate of a relationship between signal values generated by a glucose sensor and blood-glucose concentration, leading to more effective applications of glucose sensors and better treatment of diabetes patients.

As shown in the drawings for purposes of illustration, embodiments are directed to calibration methods for a glucose monitor that is coupled to a sensor set to provide continuous data recording of readings of glucose levels from a sensor for a period of time. In one particular implementation, a sensor and monitor provide a glucose sensor and a glucose monitor for determining glucose levels in the blood and/or bodily fluids of a user. However, it will be recognized that further embodiments may be used to determine the levels of other body characteristics including, for example, analytes or agents, compounds or compositions, such as hormones, cholesterol, medications concentrations, viral loads (e.g., HIV), bacterial levels, or the like without deviating from claimed subject matter. In particular implementations, a glucose sensor is primarily adapted for use in subcutaneous human tissue. However, in still further embodiments, one or more sensors may be placed in other tissue types, such as muscle, lymph, organ tissue, veins, arteries or the like, and used in animal tissue to measure body characteristics. Embodiments may record readings from the sensor on an intermittent, periodic, on-demand, continuous, or analog basis.

According to an embodiment, a blood glucose concentration in fluid may be measured based upon values of a sampled sensor signal. Also, as discussed below, it can be observed in particular embodiments that the accuracy of such measurements used to measure blood glucose concentration may decrease with increases in blood glucose concentration. Accordingly, as illustrated below, in estimating a blood glucose response of a particular sensor, measurements taken at lower blood glucose concentrations may be more heavily weighted than samples take a higher blood glucose concentrations.

Briefly, in one particular embodiment, an electrical signal generated by a sensor may be sampled to provide sample values associated with a blood-glucose concentration. Uncertainty values may be associated with individual ones of the measurements based, at least in part, on blood-glucose reference values associated with the measurements. At least some of the sample values are weighted according to a decreasing function of uncertainty values associated with the sample values. A relationship of sample values with blood-glucose concentration may then be determined based, at least in part, on the individually weighted sample values. It should be understood, however, this is merely an example embodiment and claimed subject matter is not limited in this respect.

FIGS. 1-7 illustrate a glucose monitor system 1 for use with calibration methods described herein. Glucose monitor system 1, in accordance with one particular implementation, includes a subcutaneous glucose sensor set 10 and a glucose monitor 100. Here, glucose monitor 100 may be of the type described in U.S. Patent Application Ser. No. 60/121,664, filed on Feb. 25, 1999, entitled "Glucose Monitor System." In alternative embodiments, the glucose monitor is of the type described in U.S. Pat. No. 7,324,012.

In one particular application, glucose monitor 100 may be worn by a user while connected to a surface mounted glucose sensor set 10 attached to the user's body by an electrically conductive cable 102, of the type described in U.S. Patent Application Ser. No. 60/121,656, filed on Feb. 25, 1999, entitled "Test Plug and Cable for a Glucose Monitor." In one embodiment, a sensor interface may be configured in the form of a jack to accept different types of cables that provide adaptability of the glucose monitor 100 to work with different types of subcutaneous glucose sensors and/or glucose sensors placed in different locations of a user's body. However, in alternative embodiments, such a sensor interface may be permanently connected to the cable 102. In additional alternative embodiments, a characteristic monitor may be connected to one or more sensor sets to record data of one or more body characteristics from one or more locations on or in a user's body.

According to an embodiment, glucose sensor set 10 may be of a type described in U.S. Patent Application Ser. No. 60/121,655, filed on Feb. 25, 1999, entitled "Glucose Sensor Set", or U.S. patent application Ser. No. 08/871,831, filed on Jun. 9, 1997, entitled "Insertion Set For A Transcutaneous Sensor." Glucose sensor 12 may be of a type described in U.S. patent application Ser. No. 09/101,218, filed on Feb. 25, 1999, entitled "Glucose Sensor", or described in commonly assigned U.S. Pat. Nos. 5,390,671; 5,391,250; 5,482,473; and 5,586,553; extends from the glucose sensor set 10 into a user's body with electrodes 20 of the glucose sensor 12 terminating in the user's subcutaneous tissue. See also U.S. Pat. No. 5,299,571. However, in alternative embodiments, glucose sensor 12 may use other types of sensors, such as chemical based, optical based, or the like. In further alternative embodiments, sensors may be of a type that is used on the external surface of the skin or placed below the skin layer of the user for detecting body characteristics.

According to an embodiment, glucose monitor 100 may be capable of recording and storing data as it is received from glucose sensor 12, and may include either a data port (not shown) or wireless transmitter and/or receiver (also not shown) for transferring data to and/or from a data processor 200 such as a computer, communication station, a dedicated processor designed specifically to work with the glucose monitor, or the like. In a particular implementation, glucose monitor 100 may comprise a glucose monitor as described in U.S. Pat. No. 7,324,012.

In particular applications, glucose monitor system 1 may reduce inconvenience by separating complicated monitoring process electronics into two separate devices; the glucose monitor 100, which attaches to the glucose sensor set 10; and the data processor 200, which contains the software and programming instructions to download and evaluate data recorded by the glucose monitor 100. In addition, the use of multiple components (e.g., glucose monitor 100 and data processor 200) may facilitate upgrades or replacements, since one module, or the other, can be modified, re-programmed, or replaced without requiring complete replacement of the monitor system 1. Further, the use of multiple components can improve the economics of manufacturing, since some components may require replacement on a more frequent basis, sizing requirements may be different for each module, different assembly environment requirements, and modifications can be made without affecting the other components.

Glucose monitor 100 may take raw glucose sensor data from glucose sensor 12 and assess such sensor data in real-time and/or stores it for later processing or downloading to data processor 200, which in turn may analyze, display, and log the received data. Data processor 200 may utilize the recorded data from the glucose monitor 100 to analyze and review a blood glucose history. In particular embodiments, glucose monitor 100 is placed into a com-station which facilitates downloading data to a personal computer for presentation to a physician. Software may be used to download such data, create a data file, calibrate the data, and display such data in various formats including charts, forms, reports, graphs, tables, lists and/or the like. In further embodiments, glucose monitor system 1 may be used in a hospital environment and/or the like.

In alternative embodiments, glucose monitor 100 may include at least portions of the software described as contained within the data processor 200 above. Glucose monitor 100 may further contain software enabling calibration of glucose sensor signals, display of a real-time blood glucose value, a showing of blood glucose trends, activate alarms and the like. A glucose monitor with these added capabilities is useful for patients that might benefit from real-time observations of their blood glucose characteristics even while they're not in close proximity to a computer, communication device and/or dedicated independent data processor.

As shown in FIG. 2, data processor 200 may include a display 214 adapted to display calculated results of raw glucose sensor data received via a download from glucose monitor 100. Results and information displayed may include, but is not limited to, trending information of a characteristic (e.g., rate of change of glucose), graphs of historical data, average characteristic levels (e.g., glucose), stabilization and calibration information, raw data, tables (showing raw data correlated with the date, time, sample number, corresponding blood glucose level, alarm messages, and more) and/or the like. Alternative embodiments may include an ability to scroll through raw data. Display 214 may also be used in conjunction with buttons (not shown) on the data processor 200, computer, communication station, characteristic monitor and/or or the like, to program or update data.

Glucose monitor 100 may be combined with other medical devices to accept other patient data through a common data network and/or telemetry system. Glucose monitor 100 may be combined with a blood glucose meter to directly import or correlate glucose calibration reference values such as described in U.S. patent application Ser. No. 09/334,996, filed Jun. 17, 1999, entitled "Characteristic Monitor With A Characteristic Meter and Method Of Using The Same." Glucose monitor 100 may also be combined with semi-automated medication infusion pumps of the external type, as described according to particular embodiments in U.S. Pat. Nos. 4,562,751; 4,678,408; and 4,685,903; or automated implantable medication infusion pumps, as described according to particular embodiments in U.S. Pat. No. 4,573,994. Glucose monitor 100 may record data from the infusion pumps and/or may process data from both the glucose sensor 12 and an infusion pump to establish a closed loop system to control the infusion pump based, at least in part, on glucose sensor measurements. In other embodiments, other body characteristics are monitored, and the monitor may be used to provide feedback in a closed loop system to control a drug delivery rate. In further alternative embodiments, glucose monitor 100 can be combined with a glucose sensor set 10 as a single unit.

Glucose sensors may be replaced periodically to avoid infection, decaying enzyme coating and therefore sensor sensitivity, deoxidization of the electrodes, and/or the like. Here, a user may disconnect glucose sensor set 10 from cable 102 and glucose monitor 100. A needle 14 may be used to install another glucose sensor set 10, and then the needle 14 may be removed. Further description of the needle 14 and sensor set 10 according to particular embodiments may be found in U.S. Pat. Nos. 5,586,553; 6,368,141 and 5,951,521.

A user may connect connection portion 24 of glucose sensor set 10 through cable 102 to glucose monitor 100, so that glucose sensor 12 can then be used over a prolonged period of time. An initial reading may be downloaded from the glucose sensor set 10 and glucose monitor 100 to data processor 200, to verify proper operation of glucose sensor 10 and glucose monitor 100. In particular embodiments, glucose sensor set 10 may provide data to glucose monitor 100 for one to seven days before replacement. Glucose sensors 12 may last in the user's body for longer or shorter periods of time depending on the quality of the installation, cleanliness, the durability of the enzyme coating, deoxidization of the sensor, user's comfort, and the like.

After installation into the body, glucose sensor 12 may be initialized to achieve a steady state of operation before starting a calibration process. In a particular implementation, power supplied by three series silver oxide 357 battery cells 110 in glucose monitor 100 may be used to speed the initialization of glucose sensor 12. Alternatively, other power supplies may be used such as, different battery chemistries including lithium, alkaline, or the like, and different numbers of batteries, solar cells, a DC converter plugged into an AC socket (provided with proper electrical isolation), and/or the like.

The use of an initialization process can reduce the time for glucose sensor 12 stabilization from several hours to an hour or less, for example. One particular initialization procedure uses a two step process. First, a high voltage (e.g., between 1.0-1.1 volts—although other voltages may be used) may be applied between electrodes 20 of the sensor 12 for one to two minutes (although different time periods may be used) to allow sensor 12 to stabilize. Then, a lower voltage (e.g., between 0.5-0.6 volts—although other voltages may be used) may be applied for the remainder of the initialization process (e.g., 58 minutes or less). Other stabilization/initialization procedures using differing currents, currents and voltages, different numbers of steps, or the like, may be used. Other embodiments may omit such an initialization/stabilization process, if not required by a particular body characteristic sensor or if timing is not a factor. Alternatively, a characteristic monitor or data processor 200 may apply an algorithm to the sensor data to determine whether initial transients have sufficiently diminished and the sensor is at a significantly stable state to begin calibration.

In particular embodiments, data may not be considered valid until a sensor initialization event flag (ESI) is set in data indicating that stabilization is complete. In one particular implementation, stabilization may be complete after 60 minutes or when a user enters a sensor initialization flag using one or more buttons on the glucose monitor 100. Following completion of stabilization/initialization, glucose monitor 100 may be calibrated to accurately interpret readings from the newly installed glucose sensor 12.

Beginning with the stabilization process, glucose monitor 100 may measure a continuous electrical current signal (ISIG) generated by glucose sensor 12 in connection with a concentration of glucose present in the subcutaneous tissue of the user's body. In particular embodiments, glucose monitor 100 may sample the ISIG from glucose sensor 12 at a sampling rate of once every 10 seconds, for example, as shown in FIGS. 8a-c. Examples of sampled values are labeled A-AD in FIG. 8a. At an interval rate of once per minute, the highest and lowest of the sampled values (shown in FIG. 8a as circled sampled values A, E, G, I, M, R, V, W, Y, and AB) are ignored, and the remaining four sampled values from an interval are averaged to create interval values (shown in FIG. 8b as values F', L', R', X', and AD'). At a glucose monitor memory storage rate of once every five minutes, the highest and lowest of the interval values (shown in FIG. 8b as values L' and X') are ignored and the remaining three interval values are averaged and stored in a glucose monitor memory as memory values (shown in FIG. 8c as point AD"). The memory values are retained in memory and may be downloaded to data processor 200. Such memory values may be used to calibrate glucose monitor 100 and/or post processor 200 and to analyze blood glucose levels. The sampling rate, interval rate and the memory storage rate may be varied as necessary to capture data with sufficient resolution to observe transients or other changes in the data depending on the rate at which sensor values can change, which is affected by the sensor sensitivity, the body characteristic being measured, the physical status of the user, and the like. In other embodiments, all of the sampled values are included in the average calculations of memory storage values. In alternative embodiments, more or less sampled values or interval values are ignored depending on the signal noise, sensor stability, or other causes of undesired transient readings. Finally, in still other embodiments, all sampled values and/or interval values are stored in memory.

Clipping limits may be used to limit a signal magnitude variation from one value to the next thereby reducing the effects of extraneous data, outlying data points, or transients. In particular embodiments, clipping limits may be applied to interval values. For instance, interval values that are above a maximum clipping limit or below a minimum clipping limit may be replaced with the nearest clipping limit value.

In alternative embodiments, interval values that are outside of clipping limits may be ignored and not used to calculate a subsequent memory storage value. In particular implementations, detection of interval values outside of clipping limits may be considered a calibration cancellation event. In further particular embodiments, a calibration cancellation event may be recognized if more than one value is deemed outside of clipping limits.

(Calibration Cancellation Events are Discussed Below).

In particular embodiments, clipping limits may be shifted after each data point. Here, clipping limits may be set to a level based, at least in part, on an acceptable amount of change from a previous interval value to a present interval value, which is affected by sensor sensitivity, signal noise, signal drift, and/or the like. In particular implementations, clipping limits may be calculated for a current interval based on the magnitude of the previous interval value. For example, for a previous interval value from zero up to but not including 15 Nano-Amps, clipping limits may be set at plus and minus 0.5 Nano-Amps about the previous interval value. For a previous interval value from 15 Nano-Amps up to but not including 25 Nano-Amps, clipping limits may be set at plus and minus 3% of the previous interval value, about the previous interval value. For a previous interval value from 25 Nano-Amps up to but not including 50 Nano-Amps, clipping limits may be set at plus and minus 2% of the previous interval value, about the previous interval value. For a previous interval value of 50 Nano-Amps and greater, clipping limits may be set at plus and minus 1% about the previous interval value. In alternative embodiments, different clipping limits may be used and claimed subject matter is not limited in this respect.

Figure 9:
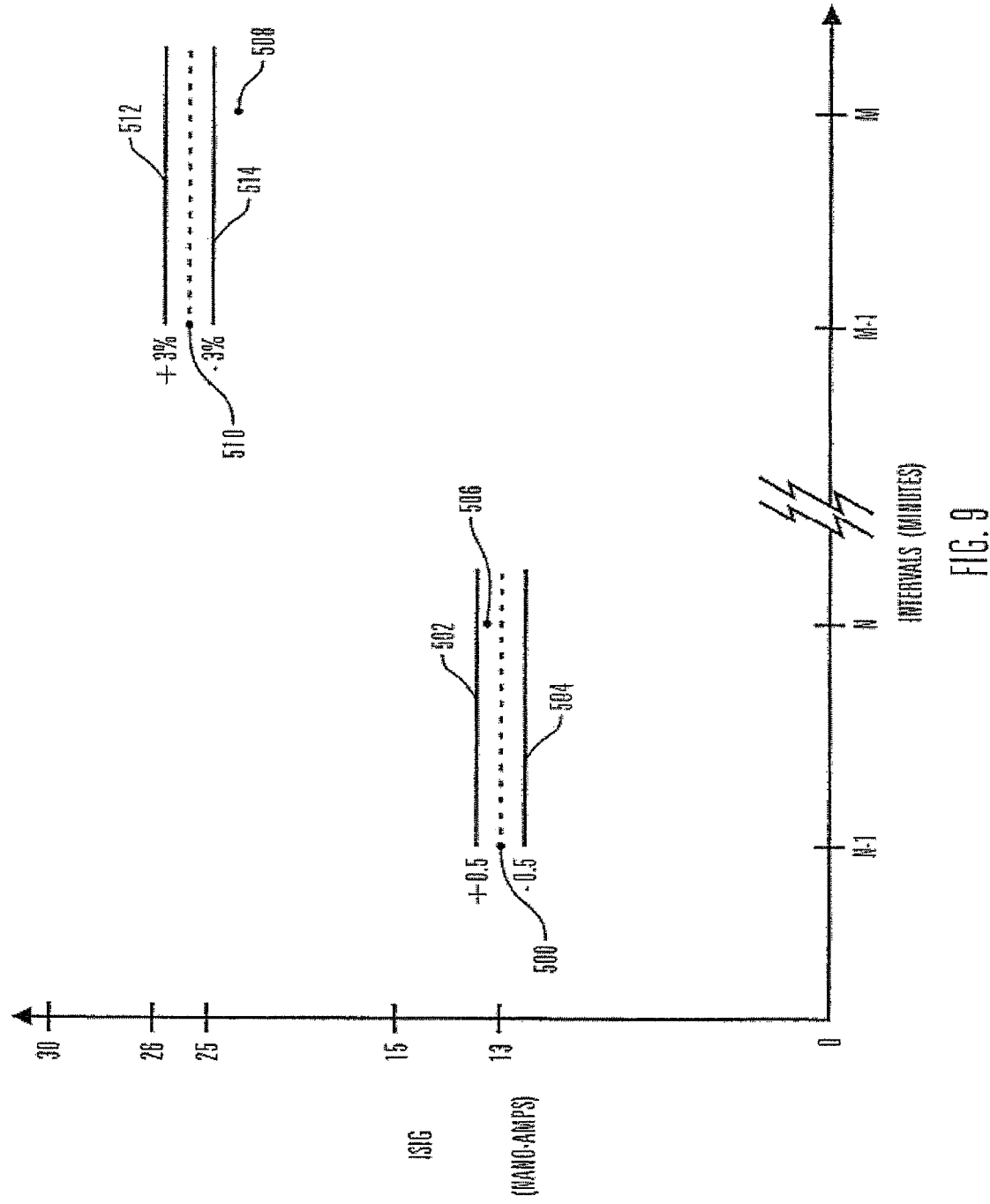
FIG. 9 is a chart showing clipping limits according to an embodiment.

FIG. 9 shows a clipping limit example according to a particular embodiment in which a previous interval value 500, associated with interval N-1, has a magnitude of 13.0 Nano-Amps, which is less than 15.0 Nano-Amps. Therefore, a maximum clipping limit 502 for a present interval value 506 is set at 13.5 Nano-Amps, which is 0.5 Nano-Amps greater than the magnitude of the previous interval value 500. A minimum clipping limit 504 is set at 12.5 Nano-Amps which is 0.5 Nano-Amps below the previous interval value 500. Present interval value 506, associated with interval N, is between the maximum clipping limit 502 and the minimum clipping limit 504 and is therefore acceptable.

In another example shown in FIG. 9, the present interval value 508, associated with interval M, has a value of 25.0 Nano-Amps which is outside of the clipping limit 514 and will therefore be clipped. The previous interval value 510, associated with interval M-1, is 26.0 Nano-Amps, which is included in the range from 25.0 up to but not including 50.0 Nano-Amps as discussed above. Therefore the clipping limits are +/−2%. The maximum clipping limit 512 is 2% greater than the previous interval value 510 as follows:

26.0+26.0*0.02=26.5 Nano-Amps.

Similarly the minimum clipping limit 514 is 2% less than the previous interval value 510 as follows:

26.0−26.0*0.02=22.5 Nano-Amps.

Figure 8:
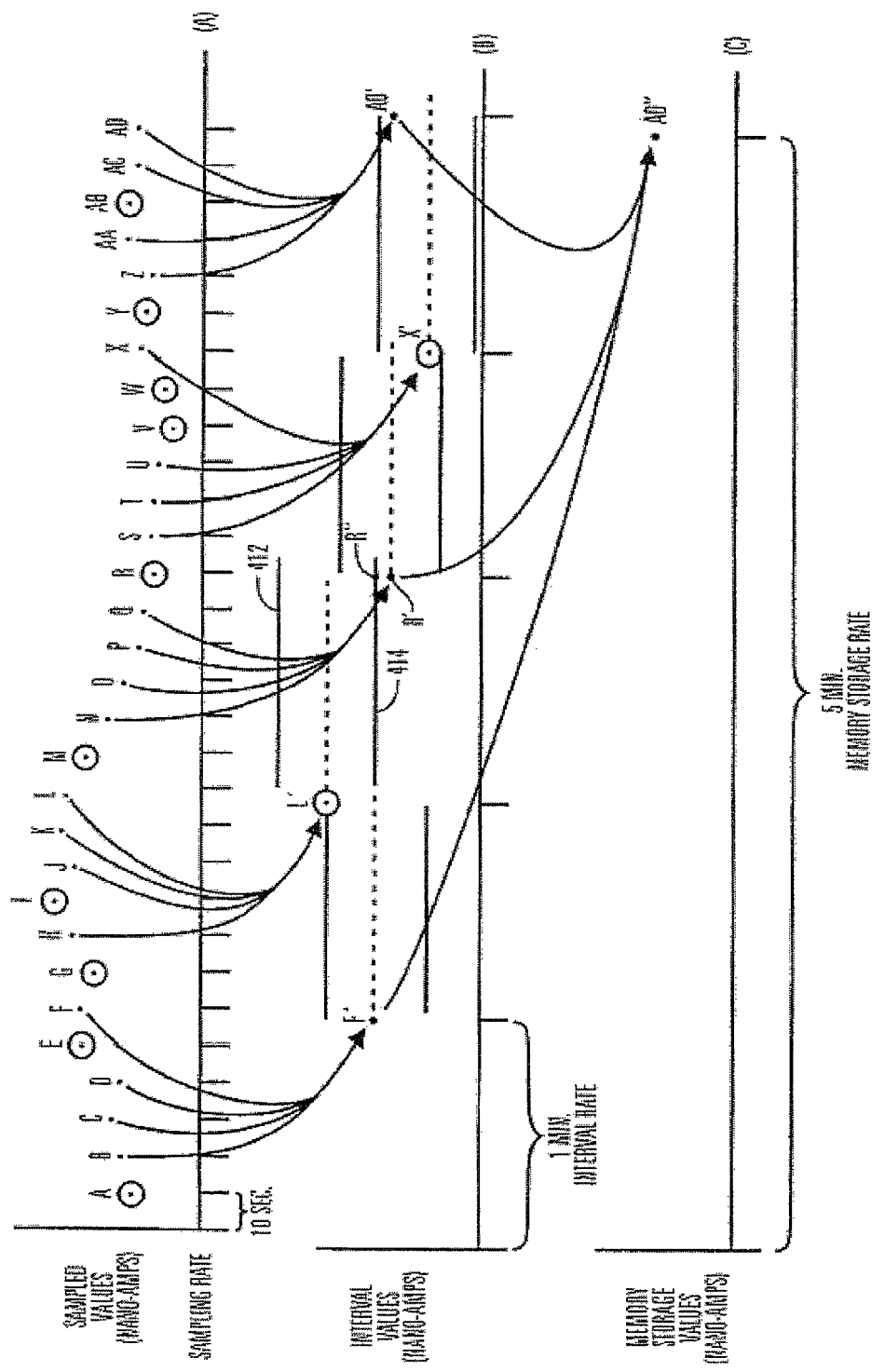
FIGS. 8a through 8c are diagrams showing a relationship between sampled values, interval values and memory storage values according to an embodiment.

Since the present interval value 508 of 25.0 Nano-Amps is less than the minimum clipping limit 514 of 25.5 Nano-Amps, it will be clipped, and 25.5 Nano-Amps will be used in place of 25.0 Nano-Amps to calculate a memory storage value. For further illustration, FIG. 8 shows interval value R', which is calculated by averaging sampled values N through Q, is outside of the clipping limits 412 and 414, which result from the previous interval value L'. Therefore, in this particular example, the magnitude of interval value R' is not used to calculate memory value AD", instead R", which is the magnitude of the minimum clipping limit 414, is used.

In other embodiments, clipping limits may be a smaller or larger number of Nano-Amps or a smaller or larger percentage of the previous interval value based on the sensor characteristics mentioned above. Alternatively, clipping limits may be calculated as plus or minus the same percent change from every previous interval value. Other algorithms may use several interval values to extrapolate the next interval value and set the clipping limits to a percentage higher and lower than the next anticipated interval value. In further alternatives, clipping may be applied to the sampled values, interval values, memory values, calculated glucose values, estimated values of a measured characteristic, or any combination of such values.

In particular embodiments, interval values are compared to an out-of-range limit of 200 Nano-Amps. If three consecutive interval values are equal to or exceed the out-of-range limit, the sensor sensitivity may be deemed to be too high, and an alarm is activated to notify the user that re-calibration is required or the sensor may need replacing. In alternative embodiments, an out-of-range limit may be set at higher or lower values depending on the range of sensor sensitivities, the expected working life of the sensor, the range of acceptable measurements, and/or the like. In particular embodiments, an out-of range limit is applied to sampled values. In other embodiments, an out-of-range limit is applied to the memory storage values.

In particular embodiments, unstable signal alarm limits may be set to detect drastic changes in memory storage values from one to another. Signal alarm limits may be established similarly to the clipping limits described above for the interval values, but allow for a larger change in value since there is more time between memory storage values than between interval values. Re-calibration or replacement of the glucose sensor 12 may be performed once an unstable signal alarm is activated. In essence, in a particular implementation, such an alarm is therefore activated in the event that glucose monitor 100 detects an unacceptable level of noise in the ISIG from glucose sensor 12.

In a particular embodiment, a memory storage value may be considered valid (Valid ISIG value) unless one of the following calibration cancellation events occurs: an unstable signal alarm (as discussed above); a sensor initialization event (as discussed above); a sensor disconnect alarm; a power on/off event; an out-of-range alarm (as discussed above); or a calibration error alarm. Here, only Valid ISIG values may be used to calculate blood glucose levels by the glucose monitor 100 or post processor 200, as shown in FIG. 10. Once a calibration cancellation event occurs, successive memory storage values are not valid, and therefore are not used to calculate blood glucose, until glucose monitor 100 or post processor 200 is re-calibrated. FIG. 10 shows an explanatory computer screen shot in which cell P3 indicates a sensor disconnect alarm with the abbreviation "SeDi". As shown, blood glucose values do not appear in column K, titled "Sensor Value", and Valid ISIG values do not appear in column J until after the sensor is initialized, as indicated by the "ESI" flag in cell N17. One exception however, is the power on/off event. If glucose monitor 100 is turned off for a short enough period of time, up to 30 minutes for example, memory storage values may be considered Valid ISIG values as soon as the power is restored. If the power is off for longer than 30 minutes, for example, glucose monitor 100 may be re-calibrated before ISIG values are considered valid. Alternatively, power may be off for a duration such as 30 minutes or longer and, once power is restored, the memory storage values may comprise Valid ISIG values. Here, a sensor disconnect alarm may be activated if the glucose monitor 100 does not detect a signal. In preferred embodiments, when two or more out of five interval values collected within a given memory storage rate are less than 1.0 Nano-Amp, a disconnect alarm may be triggered. In alternative embodiments, greater or fewer values need be below a particular threshold current level to trigger a disconnect alarm depending of the acceptable range or sensor readings and the stability of an associated sensor signal. Two remaining calibration cancellation events, the calibration error and an alternative embodiment for the out-of-range alarm, are discussed in conjunction with the calibration process below.

Particular implementations are directed to calibration techniques that may be used by either glucose monitors during real-time measurements of one or more signals from a glucose sensor, or post processors during post-processing of data that has been previously recorded and downloaded (as shown in FIG. 10).

To calibrate glucose monitor 100, a calibration factor called a sensitivity ratio (SR) (blood glucose level/Valid ISIG value) may be calculated for a particular glucose sensor 12. The SR is a calibration factor used to measure/estimate a blood glucose concentration based, at least in part on a Valid ISIG value (Nano-Amps) into a blood glucose level (mg/dl or mmol/l). In alternative embodiments, units for the SR may vary depending on the type of signal available from the sensor (frequency, amplitude, phase shift, delta, current, voltage, impedance, capacitance, flux, and the like), the magnitude of the signals, the units to express the characteristic being monitored, and/or the like.

Figure 11:
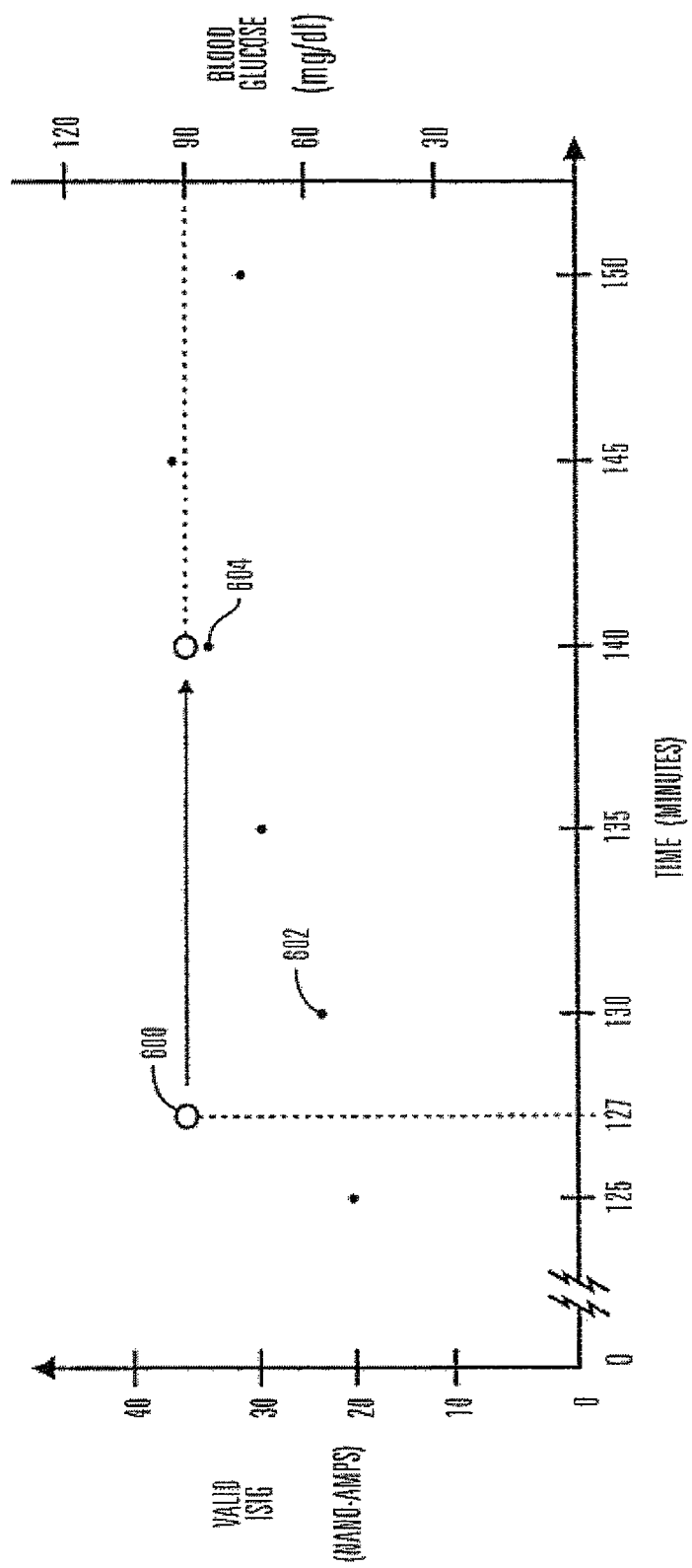
FIG. 11 is a chart illustrating the pairing of a blood glucose reference reading with glucose monitor data according to an embodiment.

In particular implementations, a user may obtain a blood glucose reference reading from a common glucose meter, or another blood glucose measuring device, and immediately enter such a blood glucose reference reading into glucose monitor 100. Such a blood glucose reference reading is assumed to be accurate and is used as a reference for calibration. Glucose monitor 100, or a post processor 200, may temporally correlate a blood glucose reference reading with a Valid ISIG value to establish a "paired calibration data point." Since a glucose level in an interstitial body fluid tends to lag behind a blood glucose level, glucose monitor 100 or post processor 200 applies a delay time and then pairs the blood glucose reference reading with a Valid ISIG value as shown in FIG. 11. In particular embodiments, an empirically derived ten minute delay may be used. In a particular implementation where Valid ISIG values are averaged and stored every five minutes, glucose monitor 100 may correlate a blood glucose reference reading with the third Valid ISIG stored in memory after the blood glucose reference reading is entered (resulting in an effective delay of ten to fifteen minutes in this particular example). FIG. 11 illustrates an example, in which a blood glucose reference reading 600 of 90 mg/dl is entered into the glucose monitor 100 at 127 minutes. The next Valid ISIG value 602 may be stored at 130 minutes. Given a 10 minute delay, a glucose reference reading 600 may be paired with Valid ISIG value 604 which is stored at 140 minutes with a value of 30 Nano-amps. Note that two numbers are needed to establish one paired calibration data point, a blood glucose reference reading and a Valid ISIG.

Other delay times may be used depending on a particular user's metabolism, response time of the sensor, delay time incurred for the glucose meter to calculate a reading and for the reading to be entered into the glucose monitor 100, a type of analyte being measured, the tissue that the sensor is placed into, environmental factors, whether the previous glucose Valid ISIG value (or the trend of the Valid ISIG values) was higher or lower than current Valid ISIG value, and/or the like. Once paired calibration data is available, the appropriate calibration process may be applied dependent on how many paired calibration data points are available since the last calibration, the total period of time that glucose sensor 12 has been in use, and the number of times glucose sensor 12 has been calibrated.

In particular embodiments, blood glucose reference readings may be entered into glucose monitor 100 periodically through out each day of use. Here, calibration may be conducted immediately after the initialization/stabilization of glucose sensor 12 and once a day thereafter. However, such calibration may be conducted more or less often depending on whether glucose sensor 12 has been replaced, whether a calibration cancellation event has occurred, the stability of glucose sensor 12 sensitivity over time, and/or the like.

In preferred embodiments, blood glucose reference readings are collected several times per day but a new calibration factor is calculated only once per day. Therefore, typically more than one paired calibration data point is collected between calibrations. In alternative embodiments, the glucose monitor is calibrated every time a new paired calibration data point is collected.

Figure 13:
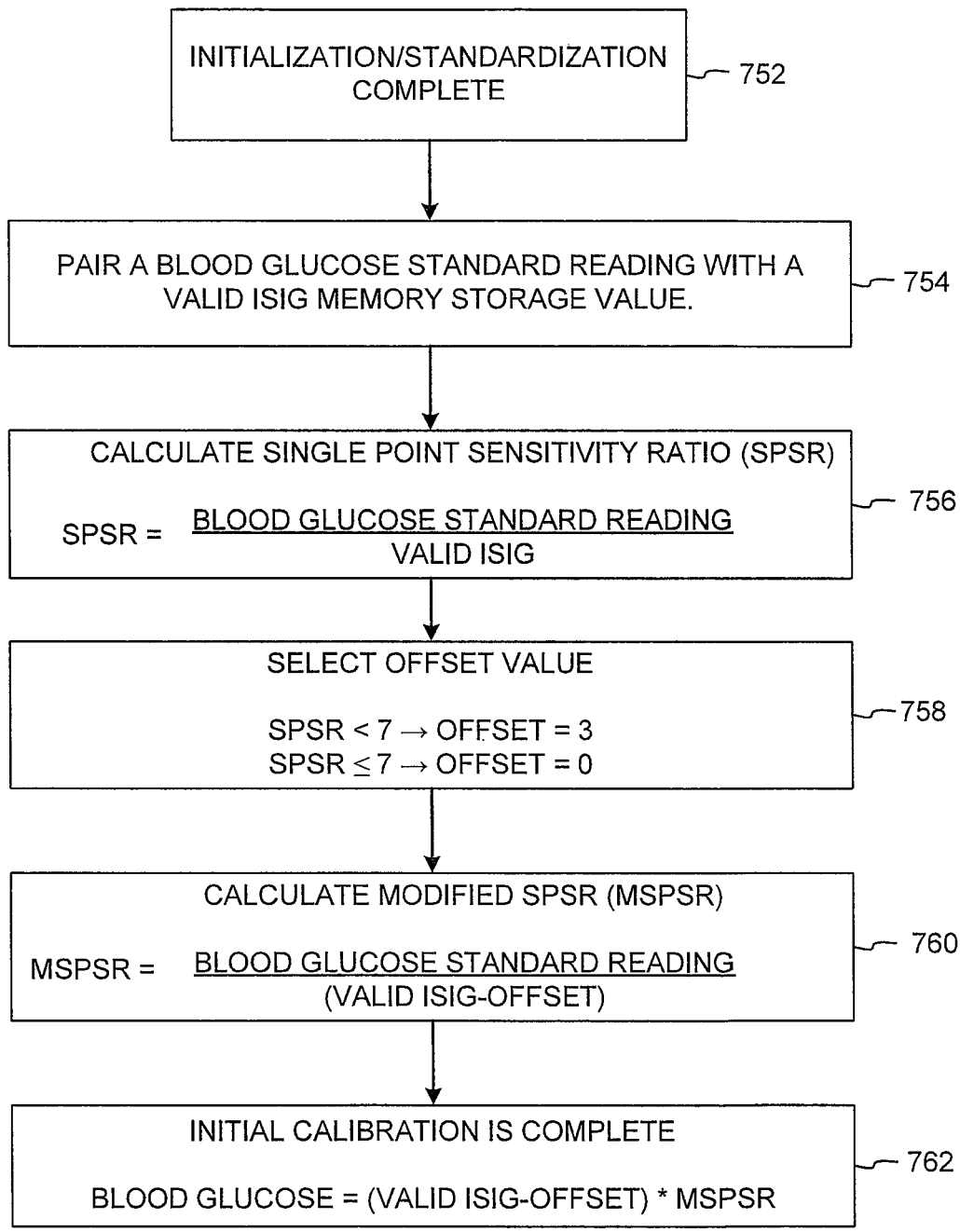
FIG. 13 is a block diagram illustrating a single-point calibration technique according to an embodiment.
Figure 15A:
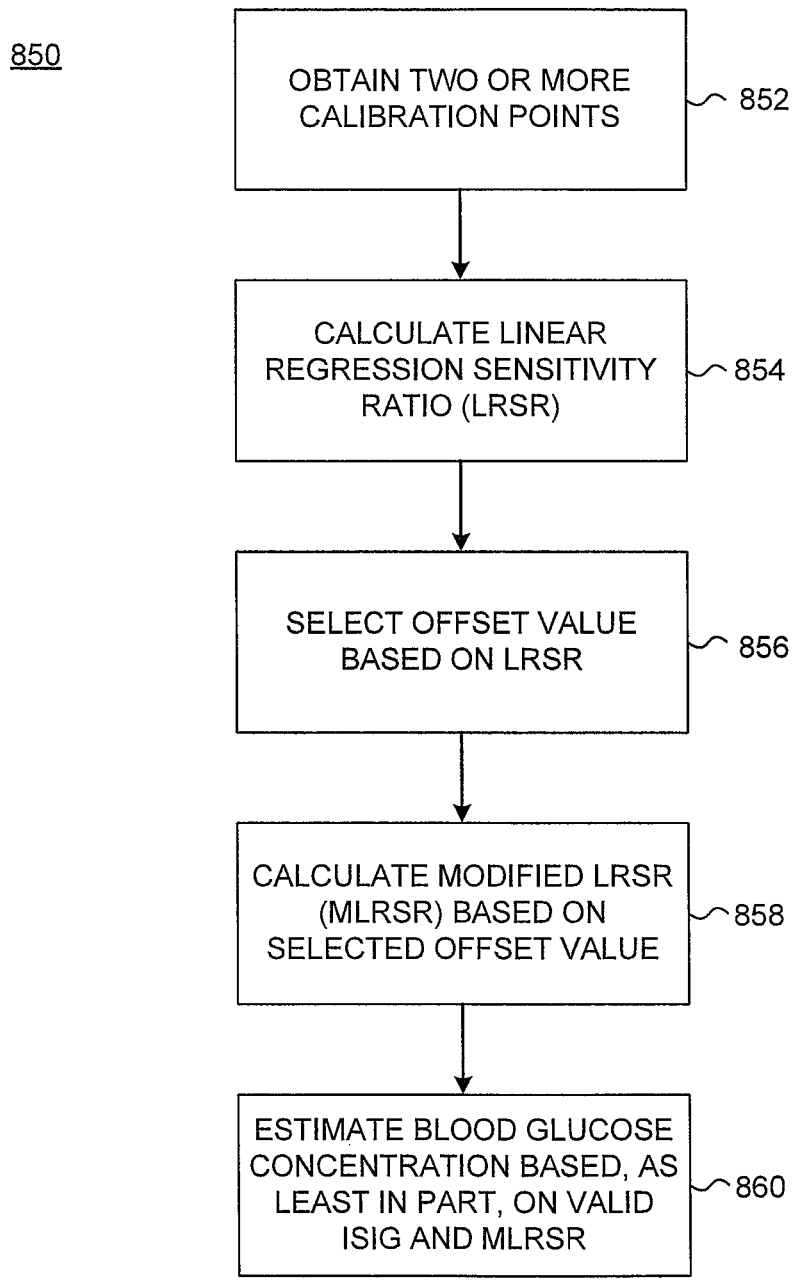
FIG. 15a is a flow diagram illustrating a calibration process according to an embodiment.

Particular embodiments may use a single-point calibration technique (shown in a block diagram of FIG. 13) to calculate the SR if only a single paired calibration data point is available, such as immediately after initialization/stabilization. And a modified linear regression technique (shown in a block diagram in FIG. 15a) may be used if two or more paired calibration data points are available. Particular embodiments may use a single-point calibration technique whether or not more than one paired calibration data point is available.

A single-point calibration equation may be based on an assumption that a Valid ISIG will be 0 when the blood glucose is 0. As shown in process 750 of FIG. 12, a single paired calibration point 700 obtained at block 754 is used with the point (0,0) to establish a line 702. The slope of the line from the origin (0,0) and passing through the single paired calibration point 700 provides a single-point sensitivity ratio (SPSR). Here, block 756 may calculate such an SPSR as follows:

$$SPSR = \frac{\text{Blood Glucose Reference Reading}}{\text{Valid } ISIG}$$

Therefore, the calibrated blood glucose level may be expressed as follows:

Blood Glucose Level=Valid ISIG*SPSR

Figure 12:
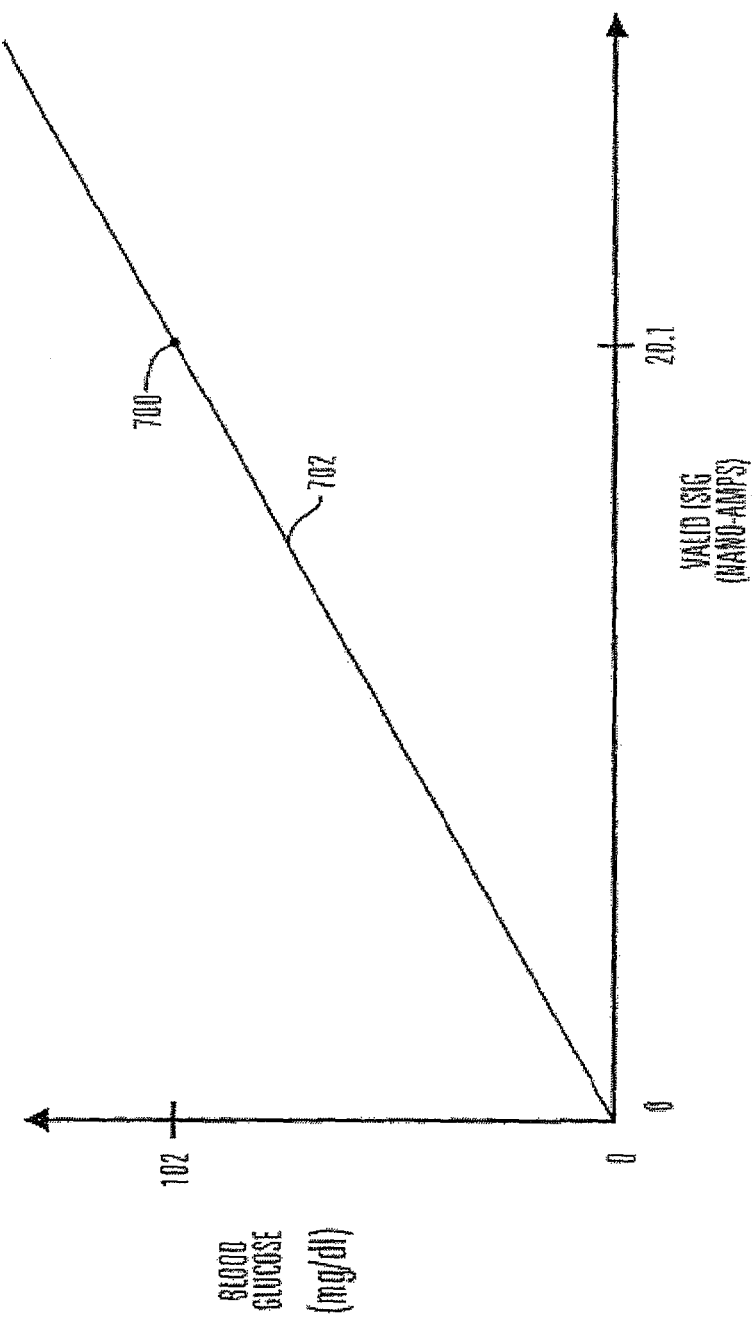
FIG. 12 is a chart illustrating an example of a single-point calibration according to an embodiment.

As an example, using the values of 20.1 Nano-Amps and 102 mg/dl from the paired calibration data point shown in FIG. 12, calculation of SPSR may be expressed as follows:

SPSR=102/20.1=5.07 mg/dl per Nano-Amp

To continue with the current example, once calibration is complete, given a glucose sensor reading of 15.0 Nano-Amps, calculated blood glucose level may be determined as follows:

Blood Glucose Level=15.0*5.07=76.1 mg/dl

Additionally, particular embodiments may use an offset value in a calibration equation to compensate for the observation that more sensitive glucose sensors 12 (e.g., glucose sensors 12 that generate higher ISIG values compared to other glucose sensors 12 at the same blood glucose level, which result in lower SR values) may have a less linear performance at very high blood glucose levels in comparison to glucose sensors 12 with lower sensitivity (and therefore relatively higher SR values). If the SPSR for a particular glucose sensor 12, as calculated above, is less than a sensitivity threshold value, then a modified SPSR (MSPSR) may be calculated at block 760 using an offset value selected at block 758. In one particular implementation, the threshold value is 7. If the initial calculation of the SPSR (shown above) is less than 7, for example, an offset value of 3 may be used to calculate the MSPSR. If the initial calculation of SPSR yields a value of 7 or greater, then the offset value may be 0. Thus, the MSPSR may be calculated at block 760 using the offset value according to a modified single-point calibration expression, as follows:

$$MSPSR = \frac{\text{Blood Glucose Reference Reading}}{\text{Valid } ISIG - \text{offset}}$$

Accordingly, an initial calibration of sensor 12 may be used to estimate a blood glucose from a sensor measurement at block 762 as follows:

Blood Glucose Level=(Valid ISIG−offset)*SPSR

Continuing the above example since the SPSR is 5.07, which is less than 7, the sensitivity ratio is recalculated using the MSPSR equation as:

MSPSR=102/(20.1−3)=5.96 mg/dl per Nano-Amp

Given a glucose sensor reading of 15.0 Nano-Amps after calibration, the calculated blood glucose may be expressed as follows:

Blood Glucose Level=(15.0−3)=5.96=71.5 mg/dl

In another example, given a blood glucose reference reading of 95 from a typical blood glucose meter and a Valid ISIG value of 22.1, a resulting SPSR may be determined as 95/22.1=4.3. Since SR<7, the offset=3. Therefore, the MSPSR is 95/[22.1−3]≈5.0. Note that if the SPSR is greater than or equal to 7 the offset value is 0 and therefore the MSPSR=SPSR. In alternative embodiments, the offset value may be eliminated from the expression for calculating the blood glucose value as follows:

Blood Glucose Level=Valid ISIG*MSPSR

The threshold value of 7 and the associated offset of 3 have been empirically selected based on the characteristics observed from testing a particular type of glucose sensors 12, such as those described in U.S. Pat. No. 5,391,250 entitled "Method of Fabricating Thin Film Sensors", and U.S. Pat. No. 6,360,888. Other threshold values may be used in conjunction with other offset values to optimize the accuracy of the calculated MSPSR for various types of glucose sensors 12 and sensors used to detect other body characteristics. In fact, many threshold values may be used to select between many offset values. An example using two different threshold values (4 and 7) to select between three different offset values (5, 3 and 0) follows:

if SPSR<4, offset=5;

if 4<SPSR<7, offset=3; and if SPSR>7, offset=0.

In particular embodiments an MSPSR may be compared to a valid sensitivity range to determine whether a newly calculated MSPSR is reasonable. In order to identify potential system problems, a valid MSPSR range of 1.5 to 15 may be employed, for example. However this is merely an example of such a range and claimed subject matter is not limited in this respect. This range may be determined based, at least in part, upon valid glucose sensor sensitivity measurements made in-vitro. MSPSR values outside this range may result in a calibration error alarm (CAL ERROR) to notify the user of a potential problem. Other valid sensitivity ranges may be applied depending on the types of sensors to be calibrated, the range of acceptable sensitivity levels for the various sensor types, the manufacturing consistency expected for the sensors, environmental conditions, how long the sensor has been in use, and/or the like.

Figure 14:
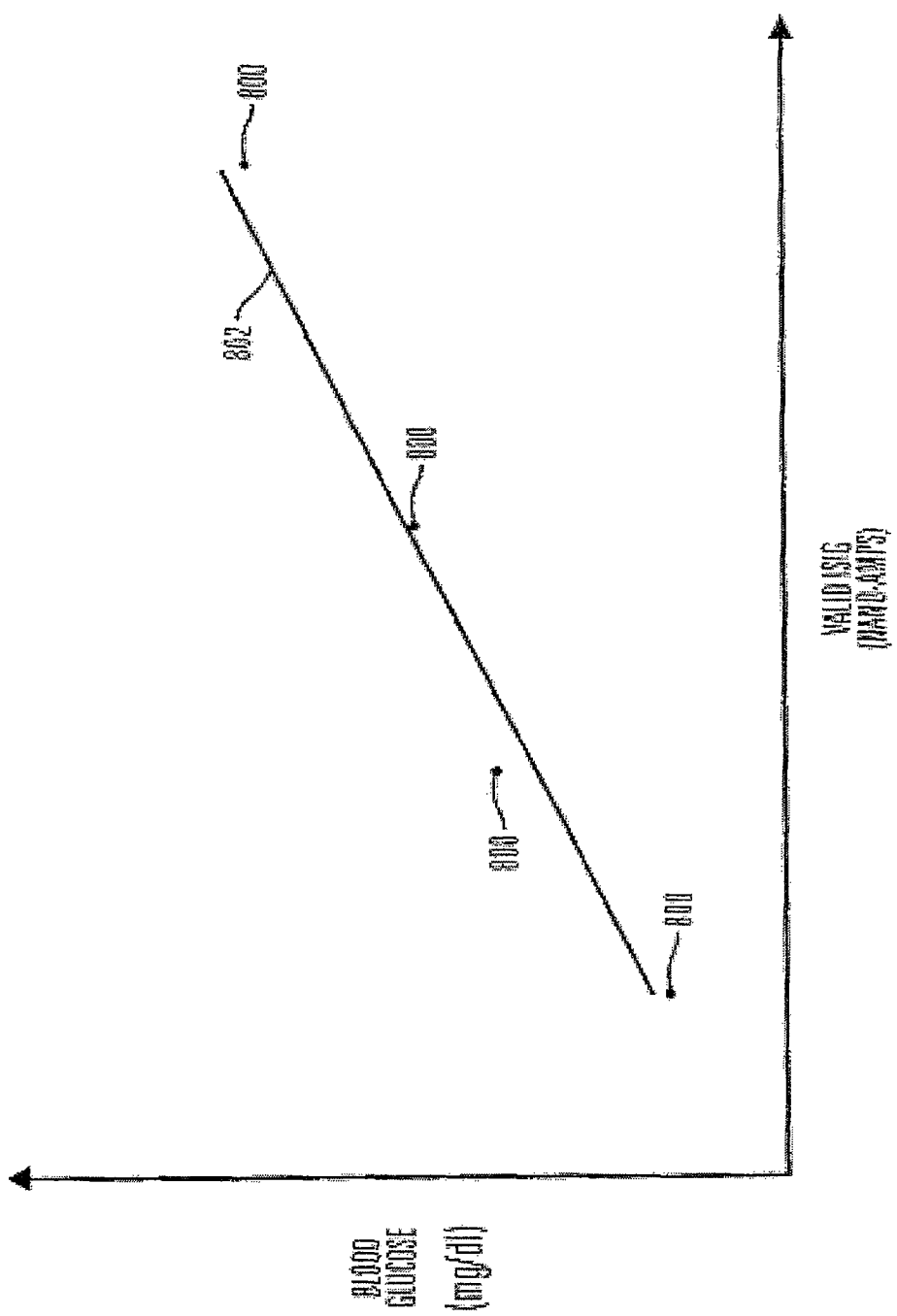
FIG. 14 is a chart illustrating an example of a linear regression calibration according to an embodiment.

Particular embodiments may augment the above described single-point calibration technique using a modified linear regression technique (shown in a block diagram in FIG. 15a) if more than one paired calibration data point is available. As shown in FIG. 14, paired calibration data points 800 may linearly regressed by a least squares method to calculate a best fit straight line 802 correlated with paired calibration data points 800. The slope of the line resulting from the linear regression may be the linear regression sensitivity ratio (LRSR) used as the calibration factor to calibrate the glucose monitor 100.

Figure 15B:
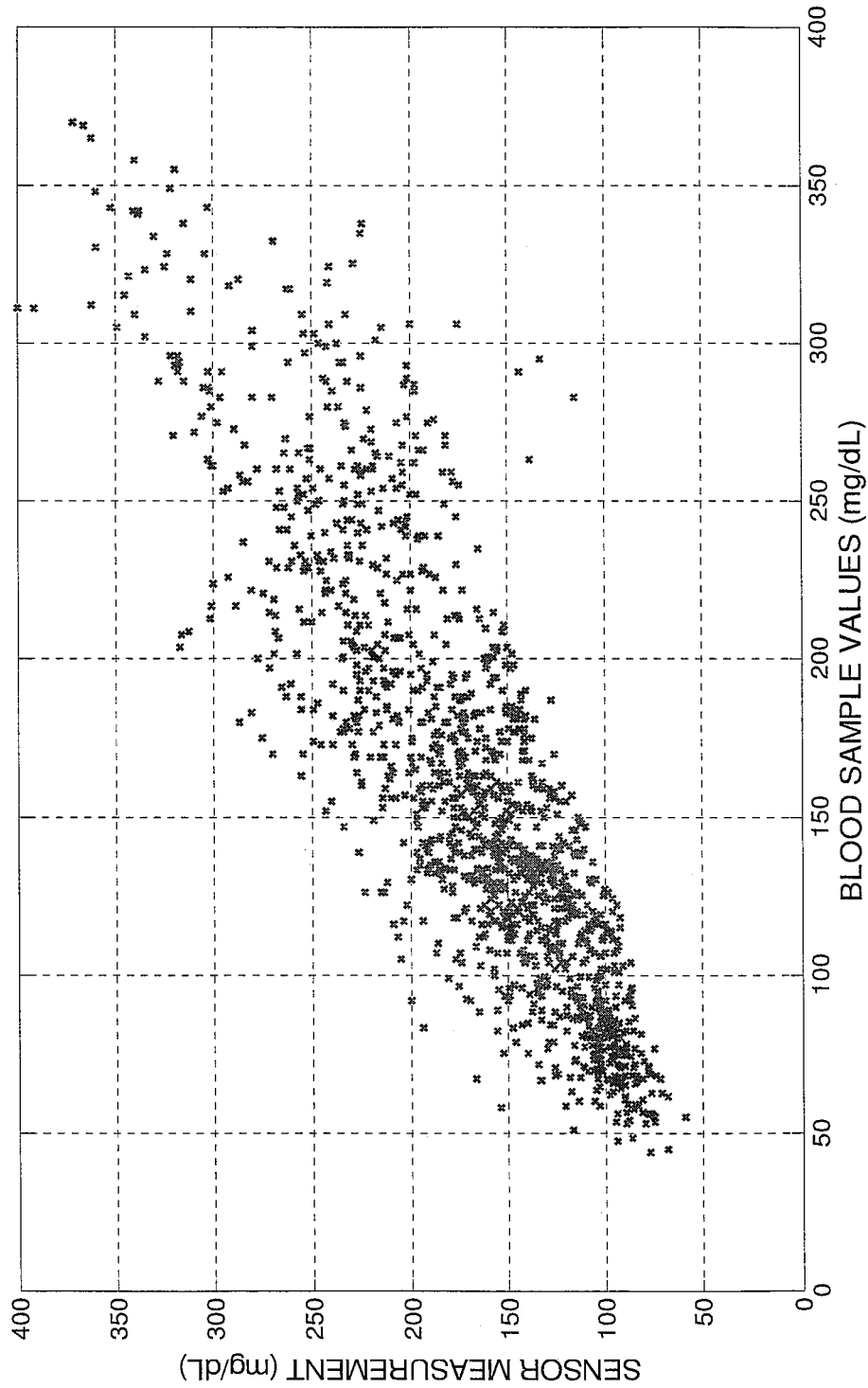
FIG. 15b is a plot of sensor measurements versus reference blood samples according to an embodiment.

Linear and nonlinear least squares regression may apply an assumption that each data point provides equal information about a deterministic part of a total variation in a value or outcome. In such processes a standard deviation of an error associated with a value would be constant for all estimated predictions, for example. In some processes this is not the case. For example, in real-time continuous glucose monitoring using an enzymatic minimally invasive biosensor to estimate plasma glucose concentrations as discussed above, an unequal error distribution may exist. Here, a scatter plot of FIG. 15b illustrates several calibrated glucose sensor points plotted against paired blood glucose reference values throughout a large glycemic range in one particular implementation. It can be observed from the plot that the accuracy of the sensor glucose measurements decreases as the reference blood glucose values increase. Such a decreasing accuracy may be measured as variance and/or standard deviation of an error associated with such measurements that increases with blood glucose concentration and/or paired reference blood glucose reference value. Accordingly, in certain circumstances it may be advantageous not to treat every observation equally, and apply a weighted least squares regression, for example. This may be implemented according to a particular embodiment by giving each point an appropriate weight to control an amount of influence over parameter determination. In doing this, points with less precise influence may be weighted less in computing a linear regression, while points with more influence may be more heavily weighted.

In a particular implementation, paired calibration points, comprising sample values associated with blood-glucose concentration sensor measurements paired with reference measurements at block 852, may be linearly regressed at block 854 to determine an LRSR. As pointed out above, in particular embodiments, such a regression may weight particular pairs and/or sample values according to a degree of certainty associated with the accuracy of such sample values based upon apriori information. Such a linear regression calibration may be computed as follows:

$$LRSR = \frac{\sum_{i=1}^{N} \alpha_i \cdot \beta_i \cdot isig_i \cdot BG_i}{\sum_{i=1}^{N} \alpha_i \cdot \beta_i \cdot isig_i^2}$$

where:
$isig_i$ is a value representing a sensor measurement of a blood glucose concentration for paired calibration point i;
$\alpha_i$ is weighting applied to paired calibration point i based upon the time that the associated sample was obtained;
$BG_i$ is reference sample of a blood glucose concentration for paired calibration point i;
$\beta_i$ is a weighting applied to paired calibration point i based upon a degree of certainty associated with accuracy of $isig_i$ as a measurement of blood glucose concentration; and
N is a number of paired calibration data points which are to be linearly regressed.

Accordingly, an estimate of a calibrated blood glucose level may be expressed as follows:

Blood Glucose Level=Valid ISIG*LRSR

In a particular implementation, a paired calibration point may be weighted according to a time associated with when associated sensor measurements and reference values are obtained. Here, for example, pairs based on more recent measurements and reference values may be associated with an error with a smaller variance than pairs based on measurements and reference values obtained in the more distant past. Accordingly, the weight $\alpha_i$ applied to calibration pairs may decrease the more distant in the past such calibration pairs are obtained.

Also, as pointed out above, variances associated with measurement errors in calibrating continuous glucose monitors may not be constant across a dynamic range of blood glucose values. Here, in one particular embodiment, weighting $\beta_i$ may represent an inverse variance weighting. In other words, contribution of each data point may be weighted with the inverse of the variance for that set of blood glucose values. For example, a set of sensor current values were paired (N=90, 000 points) and the inverse variance of sensor current calculated for each blood glucose reference value as follows:

$$\beta_i = [\text{var}(isig_i)]^{-1}$$

Here, application of such an inverse variance to calibration pairs to weight samples for linear regression is merely one example of how such calibration pairs may be weighted based upon a decreasing accuracy of sensor measurements, and claimed subject matter is not limited in this respect. Furthermore, it should be understood that a variance or standard deviation are merely examples of how a statistical dispersion of sensor measurement errors may be quantified, and that other metrics may be used. In alternative embodiments, for example, $\beta_i$ may be derived as the inverse of an estimate or approximation of the variance of $isig_i$. Also, as discussed below, appropriate weights may be derived from other functions for determining a weight based, at least in part, on blood glucose reference samples and/or blood glucose concentration.

Figure 15C:
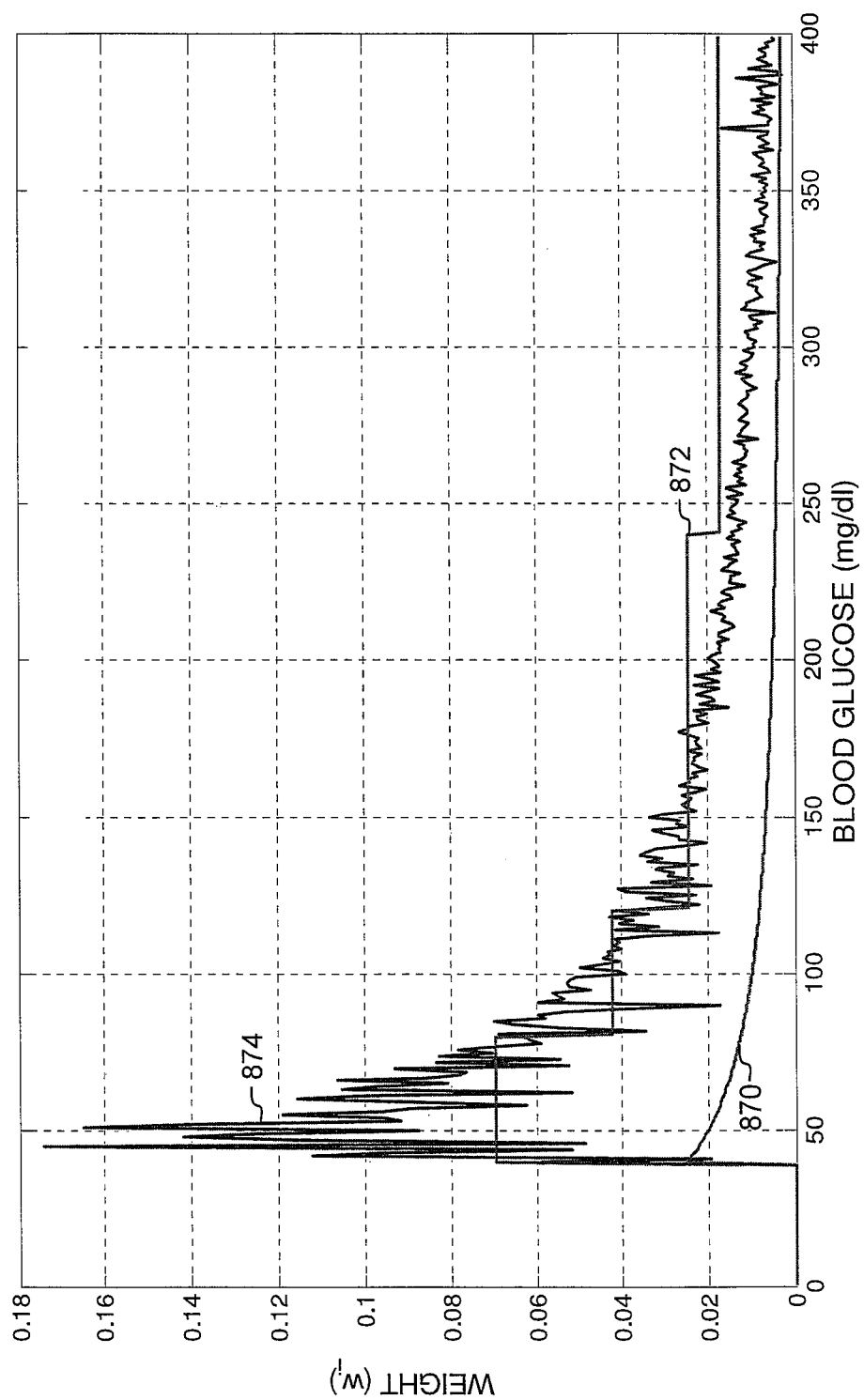
FIG. 15c is a plot of an inverse variance of sensor measurements versus blood glucose concentration according to an embodiment.

In this particular implementation, however, $\beta_i$ represents an inverse variance and/or standard deviation of all sensor samples ($isig_i$) measured at a time corresponding to when reference blood glucose sample values i were acquired. In one particular example, inverse variance weights are plotted in FIG. 15c for blood glucose values ranging from 40-400 mg/dL. Again, it should be understood, however, that the use of an inverse variance is merely one example of how calibration pairs may be weighted based upon a degree of certainty associated with accuracy of sensor measurements and claimed subject matter is not limited in this respect.

Figure 15D:
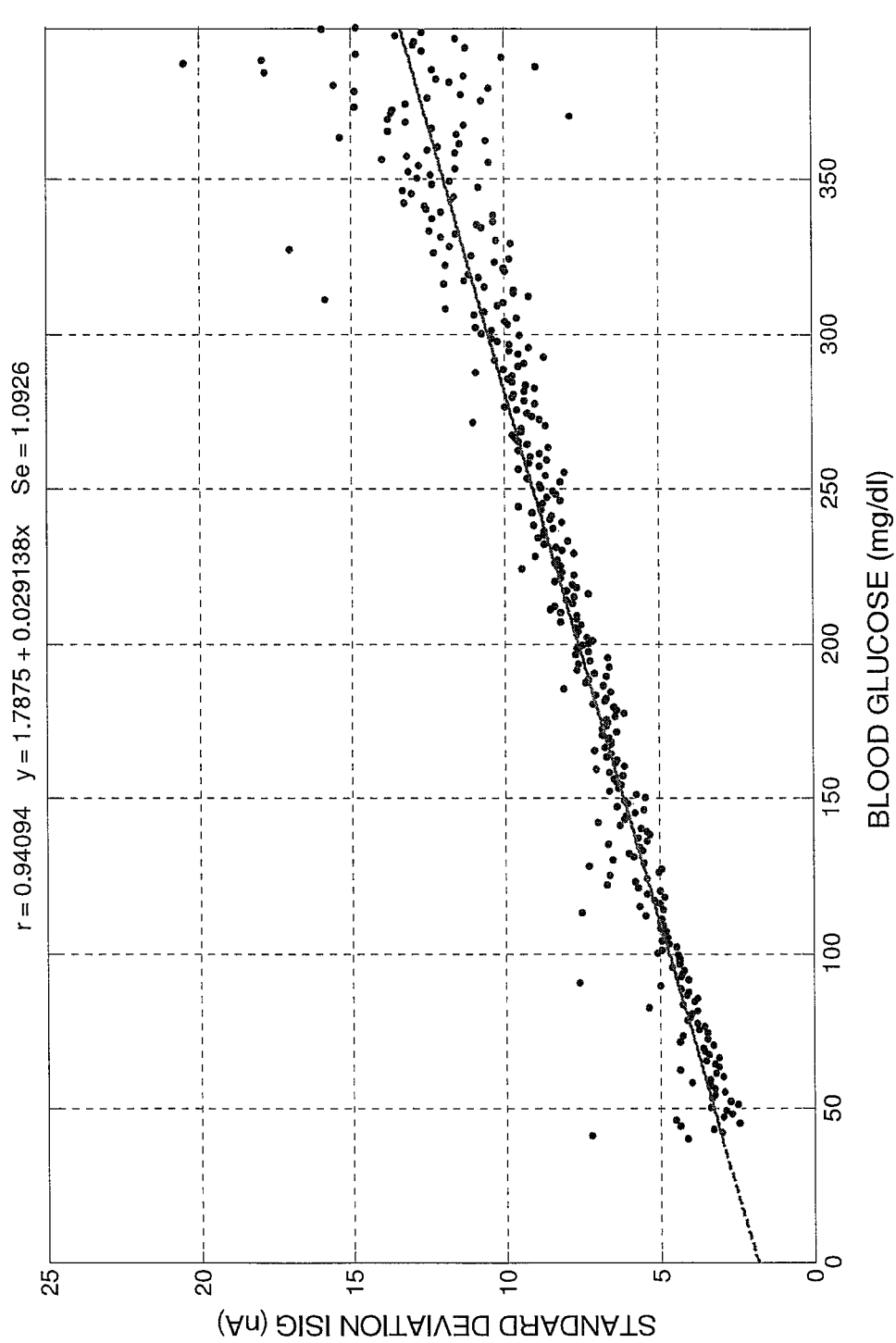
FIG. 15d is a plot illustrating a linear best fit of a standard deviation of sensor measurements versus blood glucose concentration according to an embodiment.

Alternatively, weights (for application to calibration pairs in a linear regression) may be obtained from a function based on an inverse variance weights. Here, use of such a function may provide a high quality estimate that removes noise present in the inverse variance weights arising from sources such as, for example, variability between blood-glucose and a blood glucose monitor. This is illustrated in FIG. 15d where a best line fit is produced by regressing the square root of the variance or standard deviation. For the particular example of sensor measurement samples shown in FIG. 15b, weights may be determined according to the corresponding function derived from such a best line fit as follows:

$$w_i = \frac{1}{(1.787 + 0.0291 \cdot i)^2}$$

Figure 15E:
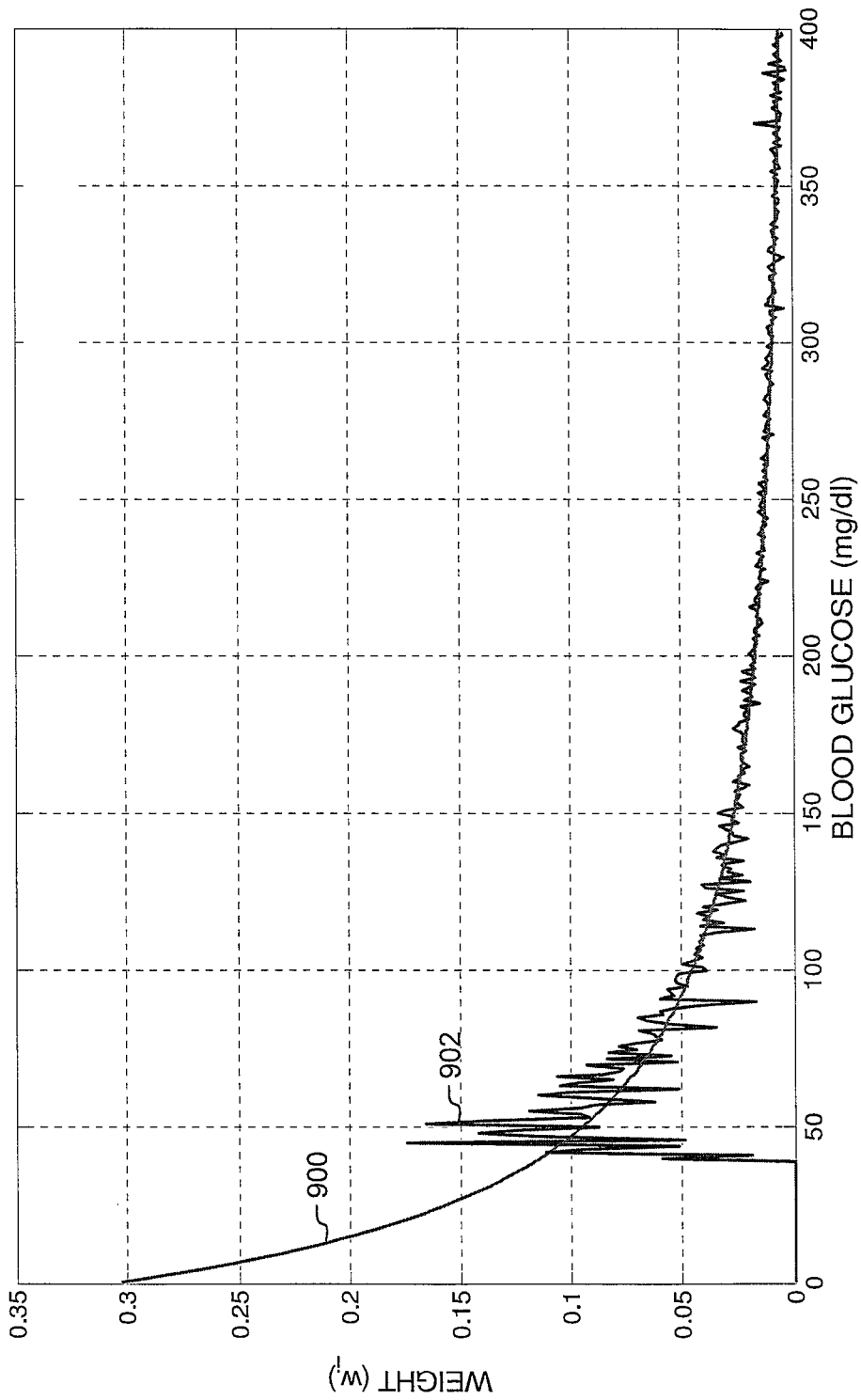
FIG. 15e is a plot of a function for obtaining weights to be applied to sensor sample values according to an embodiment.

FIG. 15e shows a plot of inverse variance $\beta_i$ and function derived from such a best line fit of variance/standard deviation as a function of ISIG weights $w_i$ over a range of blood glucose concentration range from 0 to 400 mg/dl. An inverse variance is plotted as 902 while a weighting function is plotted as 900. As can be observed, the weighting function 900 removes noise in the inverse variance to provide a weighting function to be applied to calibration pairs that is a decreasing function of blood glucose concentration and/or associated blood sample reference values associated with such calibration pairs.

It should be observed that this particular linear regression uses a fixed intercept of zero. In other words, if the Valid ISIG is 0 the blood glucose value is 0. Accordingly, this particular linear regression method estimates only one regression parameter, the slope. In alternative embodiments, other linear regression methods may be used that estimate additional regression parameters such as an offset value.

At block 856, particular embodiments may select an offset value for use in calculating a modified linear regression calibration. The purpose of such an offset value, as described above for the single-point calibration, is to compensate for an observation that more sensitive glucose sensors 12 may have a less linear performance at very high blood glucose levels. If an LRSR for a particular glucose sensor 12, as calculated in the linear regression calibration expression above, is less than a sensitivity threshold value, then a modified linear regression sensitivity ratio (MLRSR) may be calculated using an offset value included in a modified linear regression calibration expression. In one particular embodiment, for example, such a sensitivity threshold may be 7. Here, if an initial calculation of an LRSR is less than 7, an offset value of 3 may be used to calculate an MLRSR. If an initial calculation of LRSR yields a value of 7 or greater, an offset value of 0 may be used. Thus, MLRSR may be calculated at block 858 using the selected offset value in the modified linear regression calibration according to the following expression:

$$MLRSR = \frac{\sum_{i=1}^{N} \alpha_i \cdot \beta_i \cdot [isig_i - \text{offset}] BG_i}{\sum_{i=1}^{N} \alpha_i \cdot \beta_i \cdot [isig_i - \text{offset}]^2}$$

Accordingly, a calculated blood glucose level may be estimated at block 860 as follows:

Blood Glucose Level=(Valid ISIG−offset)*MLRSR

Just as in the case of single-point calibration techniques described above, other threshold values may be used at block 856 in conjunction with other offset values in the modified linear regression calibration equation to optimize the accuracy of the calculated MLRSR for various types of glucose sensors 12 and other characteristic sensors.

In particular embodiments, a newly calculated MLRSR may be compared to a valid sensitivity range to determine whether the newly calculated MLRSR is reasonable. To identify potential system problems, a valid MLRSR range of 2.0 to 10.0 may be employed. MLRSR values outside this range may result in a calibration error alarm (CAL ERROR) to notify a user of a potential problem. As described above for the single-point calibration techniques, other valid sensitivity ranges may be applied.

In particular embodiments, glucose monitor data (e.g., paired calibration data points as discussed above) may be linearly regressed over a 24 hour period (or window), and new sensitivity ratios may be used for each 24 hour time period. In other embodiments, a time period may be reduced to only a few hours or enlarged to cover the entire monitoring period with the glucose sensor (e.g., several days—or even weeks with implanted sensors). In further embodiments, such a time window may be fixed at a predetermined size, such as 24 hours, 12 hours, 6 hours, and/or the like, and the window is moved along over the operational life of the sensor.

In particular embodiments, paired calibration data points from measurements taken before the last calibration may be used to calculate a new sensitivity ratio. For example, to calibrate the glucose monitor every 6 hours, a paired calibration data point may be established every 6 hours. A linear regression technique described above may be executed using four paired calibration data points, the most recently acquired point and points obtained from six, twelve and eighteen hours before. Alternatively, a number of paired calibration data points used in the calibration may be as few as one or as large as the total number of paired calibration data points collected since the glucose sensor was installed. In alternative embodiments, a number of paired calibration data points used in a calibration computation may grow or shrink during the life of the glucose sensor due to glucose sensor anomalies.

In still other embodiments, decay characteristics of glucose sensor 12 over time may be factored into the equation to account for known degradation characteristics of glucose sensor 12 due to site characteristics, enzyme depletion, body movement, and/or the like. Considering these additional parameters in the calibration equation may more accurately tailor calibration computations used by the glucose monitor 100 or post processor 200. In particular embodiments, other parameters may be measured along with the blood glucose such as, temperature, pH, salinity, and/or the like. These other parameters may be used to calibrate the glucose sensor using non-linear techniques.

Figure 16:
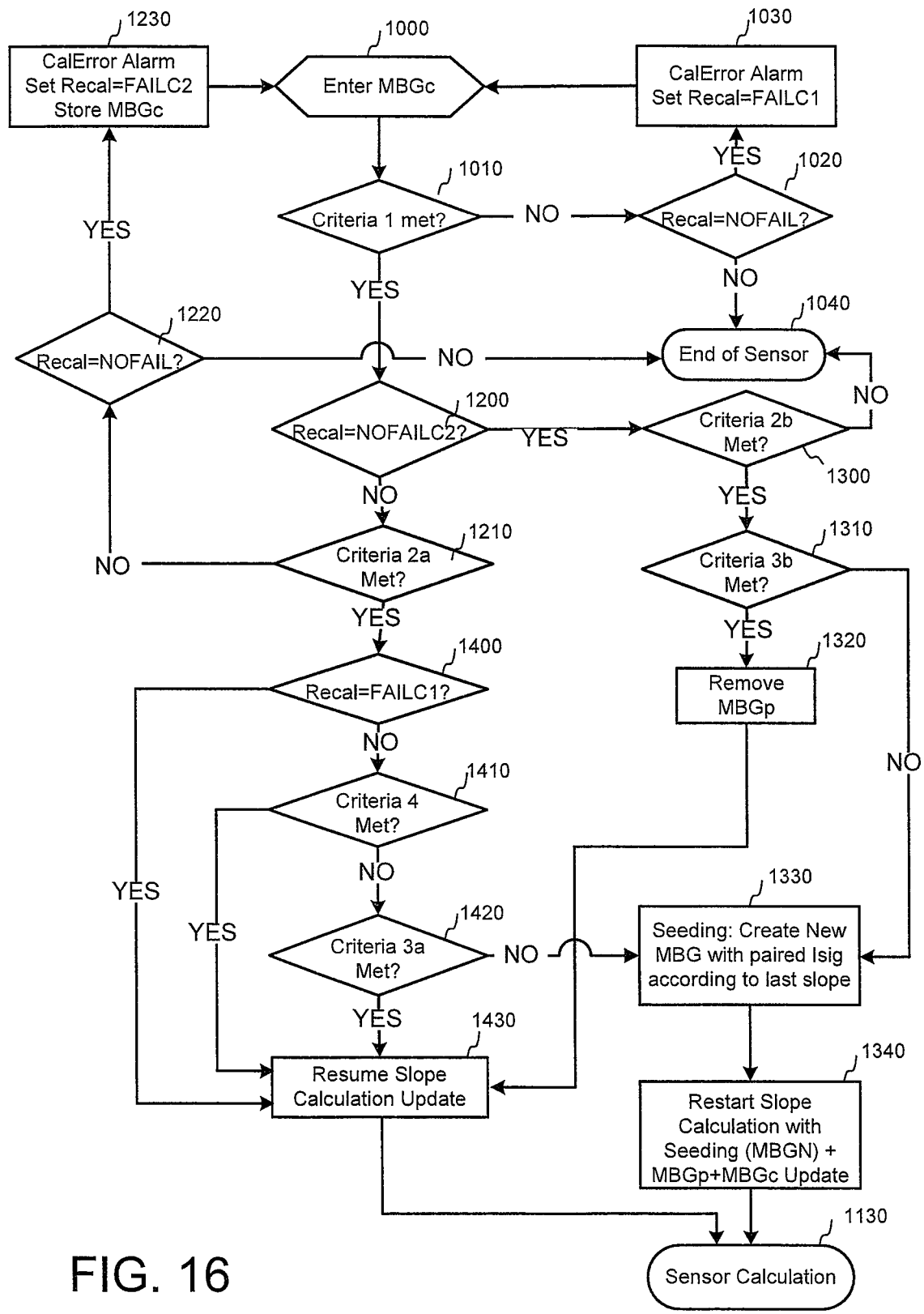
FIG. 16 is a flowchart of a self-adjusting calibration technique in accordance with an embodiment.

In a particular embodiment, real-time calibration adjustment can be performed to account for changes in the sensor sensitivity during the lifespan of the glucose sensor 12 and to detect when a sensor fails. FIG. 16 (in conjunction with FIGS. 17, 18a and 18b) describes the logic of a self-adjusting calibration technique to adjust the calibration formula or detect a sensor failure in accordance with one particular implementation.

At block 1000, a user may obtain a blood glucose reference from a common glucose meter, or another blood glucose measuring device, and immediately enter the blood glucose reference reading into glucose monitor 100. For every such meter blood glucose entry, an instantaneous calibration check may be performed and compared to an expected range of the value of the calibration check, as in block 1010. In particular embodiments, a Calibration Factor current is calculated (e.g., CFc=Meter BG/current ISIG value) to determine if the CFc (Calibration Factor current) ratio is between 1.5 to 12 ("Criteria 1"), one criterion for an accurate ISIG value in a particular implementation. If data is outside this range, raising a likelihood of a sensor failure or incorrect determination/entry of a meter BG value, a Cal Error alarm may be triggered at block 1030 and the Recalibration Variable (Recal), which is originally set at NOFAIL may be changed to FAILC1. At this point, another blood glucose reference reading may be requested and entered into the glucose monitor 100 to determine whether there was indeed a sensor failure or the Meter Blood Glucose value was incorrectly inputted. The previous Metered Blood Glucose value that generated the error can be thrown out completely. If Criteria 1 is again not satisfied at block 1010, an end of the sensor life message may be generated at block 1040 since then the Recal variable would be recognized as FAILC1 at block 1020. However, if Criteria 1 is met at block 1010, then block 1200 may determine whether the Recal variable is not equal to FAILC2. Here, the Recal variable is set to FAILC2 only if Criteria 2a is not met, which is discussed below. Given that the Recal variable at this point may only be set to a NOFAIL or FAILC1, logic proceeds to block 1210.

Block 1210, a check is performed to determine whether an existing calibration slope estimation (Previous Estimated Slope or PES) is much different from the CFc performed using a new meter blood glucose value. A significant difference may indicate a sensor failure, for example. In a particular embodiment, a difference between a previous estimated slope (PES) and a CFc in terms of percentage (threshold 1) and mg/dl (threshold 2) may be performed. Thresholds 1 and 2 may be set depending on particular sensor characteristics. In a particular implementation, an example of checking such changes between the PES and CFc may be performed as follows:

$$|1-PES/CFc|*100 > \text{threshold 1; and}$$

$$|CFc-PES|*isig > \text{threshold 2}.$$

If threshold 1 and/or threshold 2 are exceeded according to the above expressions (collectively "Criteria 2a"), then depending on the Recal variable (at block 1220), either trigger an end of sensor message may be triggered at block 1040 (if the Recal variable is equal to FAILC1 or FAILC2 at block 1220) or a Cal Error alarm may be generated at block 1230 (if the Recal variable is equal to NOFAIL at block 1220). Here, if a Cal Error alarm is generated at block 1230, the Recal variable may be set to FAILC2, the current meter blood glucose reading will be stored as MBGp (Meter Blood Glucose previous), and another blood glucose reference is requested and entered into the glucose monitor 100 (as MBGc) at block 1000. By requesting a new meter blood glucose reading, a comparison can be made between the last meter blood glucose reading stored at block 1230, and the new meter blood glucose reading entered at block 1000 may be used to determine whether there was a sensor failure. The logic follows the same paths as described above after block 1000 until the logic reaches block 1200. At block 1200, since Recal variable is now set to FAILC2 at block 1230, a difference between the previous calibration check (CFp), which generated the FAILC2 alert, and the CFc is performed at block 1300. In particular implementations, the difference between the previous calibration check and the current calibration check in terms of percentage (threshold 1) and mg/dl (threshold 2) may also be performed. In addition, a check is performed to determine whether there has been a directional change between the CFp and CFc (collectively "criteria 2b"). An example of criteria 2b may be expressed as follows:

$$|1-CFp/CFc|*100 > \text{threshold 1;}$$

$$|CFc-CFp|*Isig > \text{threshold 2; and}$$

$$(CFp-PES)*(CFc-CFp) > 0.$$

If the percentage and absolute difference exceeds threshold 1 and threshold 2, and there is no directional change in the slope with the second blood glucose meter reading, then an end of sensor message will be triggered at block 1040. If criteria 2b is met, then the logic proceeds to block 1310. At block 1310, the logic then determines whether the difference between the previous value and the current value was due to a change in sensitivity of the sensor or whether the reading is merely noise. In the preferred embodiment, the determination of change in sensitivity versus noise is made by using Criteria 3b. Criteria 3b compares the difference between (the PES and CFc) and (the CFp versus the CFc) at block 1420. For example:

$$|PES-CFc| < |CFp-CFc|$$

Figure 17A:
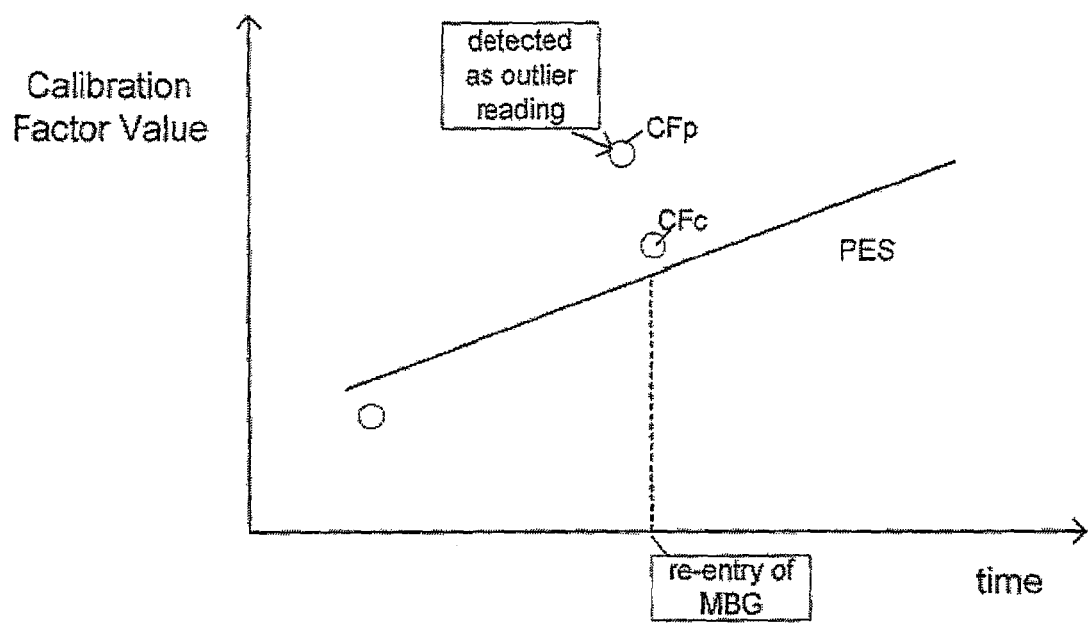
FIGS. 17a and 17b are charts illustrating an example of the self-adjusting calibration technique according to an embodiment.

As illustrated in FIG. 17a, if a difference between PES and CFc is less than a difference between CFp and CFc, criteria 3b will be met, indicating that the previous CFp is an outlier reading (e.g., an anomaly). Then, the MBGp (Meter Blood Glucose previous) is removed at block 1320 and only the MBGc paired with a valid ISIG is used in the slope calculation, which is resumed at block 1430 and applied in interpreting the sensor readings at block 1130.

Figure 17B:
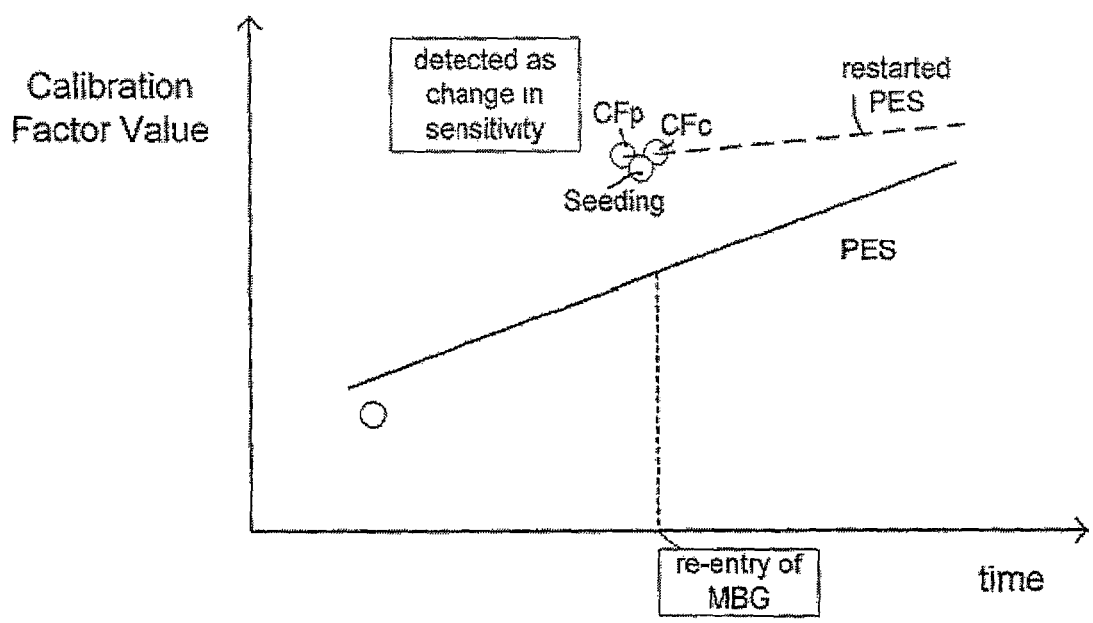

As illustrated in FIG. 17b, if criteria 3b shows that a difference between the PES and CFc is greater than a difference between CFp and CFc, criteria 3b would not be met, indicating a change in sensor sensitivity. A slope calculation may then be fine-tuned by creating a new (artificial) meter blood glucose value (MBGN) with a paired ISIG according to the last slope (Seeding) at block 1330. Using the new paired MBG (MBGN) with the paired MBGp and MBGc, the slope calculation may be restarted (or reset) at block 1340, as seen in FIG. 17b. Sensor calculation may then be performed using a new slope calculation at block 1130. By resetting a slope calculation, such a slope calculation can thus be modified automatically to account for changes in sensor sensitivity.

Continuing the logic from block 1210, if the percentage and/or absolute difference between the PES and CFc is within threshold 1 and/or threshold 2 at block 1210, indicating a valid calibration, the Recal variable is again checked at block 1400. If the Recal variable is equal to FAILC1 (indicating that the meter BG was checked twice), any fine-tuning determination may be skipped and the MBGc may be paired with a valid ISIG for use in updating a slope calculation at block 1430 and applied in interpreting sensor readings at block 1130. If the Recal Variable is not equal to FAILC1, then the logic may decide whether fine-tuning the slope calculation is needed at blocks 1410 and 1420. In particular embodiments, a decision to fine-tune may be first made by comparing a percentage and/or absolute difference between the PES and CFc (as done in block 1210) with a threshold 3 and/or a threshold 4 ("Criteria 4") at block 1410 as follows:

$$|1-PES/CFc|*100<threshold\ 3;\ and$$

$$|CFc-PES|*isig<threshold\ 4.$$

Again, threshold 3 and 4 may be determined based, at least in part, on particular sensor characteristics. If a percentage and/or absolute difference between PES and CFc is less than threshold 3 and/or threshold 4 at block 1410 (i.e. Criteria 4 met), then the slope calculation can simply be updated with the new MBGc and paired ISIG value at block 1430, and applied in interpreting the sensor readings at block 1130.

On the other hand, if the Criteria 4 is not met at block 1410, block 1420 may determine whether the difference between the expected value and the current value was due to a change in sensitivity of the sensor or whether the reading is merely noise. In one particular implementation, such a determination of change in sensitivity versus noise may be made by using Criteria 3a. Here, criteria 3a CFc and a CFp at block 1420 as follows:

$$|PES-CFp|<|CFc-CFp|$$

Figure 18A:
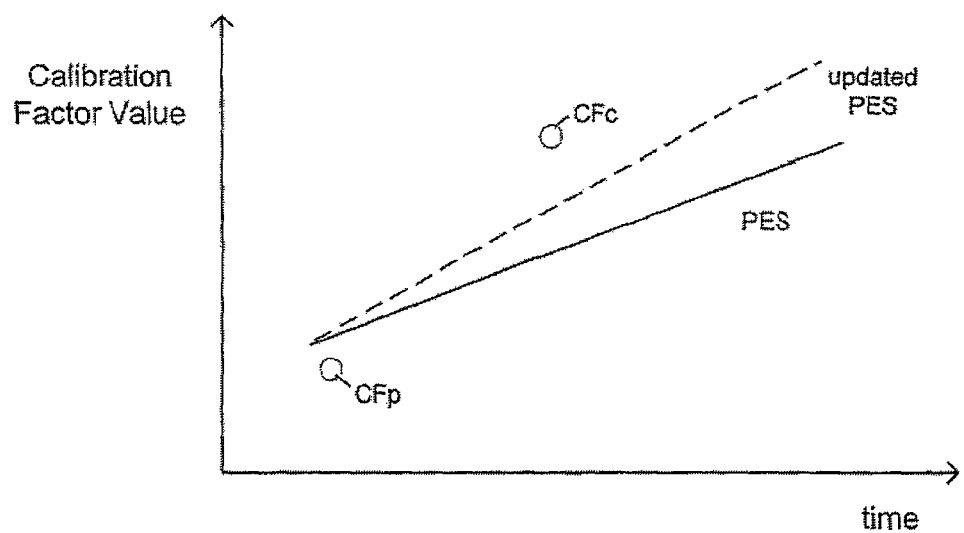
FIGS. 18a and 18b are further charts illustrating an example of the self-adjusting calibration technique according to an embodiment.

As seen in FIG. 18a, if the difference between a PES and CFp is less than a difference between CFc and the CFp, criteria 3a may be met, indicating that an error between predicted and actual values for the CFc was due to noise in previous calibrations or beginning of a change in sensor sensitivity which may be picked up in a subsequent calibration cycle. Slope calculation may then be updated with a new paired blood glucose entry (MBGc) at block 1430 and applied in interpreting sensor readings at block 1130.

Figure 18B:
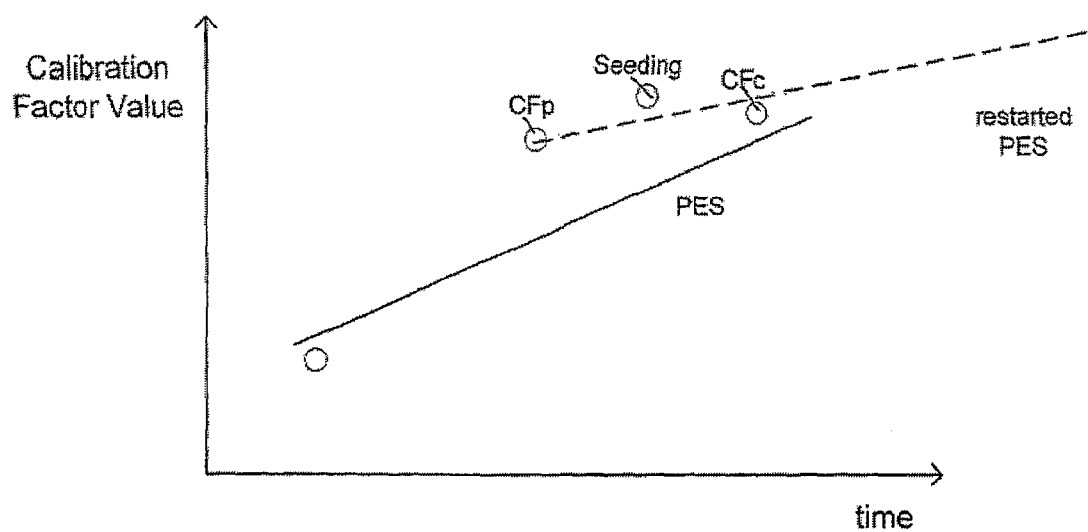

As seen in FIG. 18b, if criteria 3a shows that a difference between the PES and the previous valid calibration check is greater than a difference between the previous valid CFp and the CFc, criteria 3b would not be met, indicating a change in the sensor sensitivity and fine tuning is performed. Here, such fine tuning may be performed if two MBG entries in succession indicate a change in slope. Slope calculation may be fine-tuned by creating a new (artificial) MBGN with a paired ISIG according to the last slope (Seeding) at block 1330. Using such a new paired MBGN with the paired MBGp and MBGc, a slope calculation may be restarted (or reset) at block 1340, as seen in FIG. 18b. The sensor calculation may then be performed using the new slope calculation at block 1130. Again, by resetting the slope calculation, the slope calculation can thus be modified automatically to account for changes in sensor sensitivity.

Although the above description described the primary calibration techniques in particular embodiments, many modifications can be made to the above described calibration techniques without deviating from claimed subject matter. For example, in alternative embodiments, a calibration factor may be calculated by first using a single-point technique to calculate an MSPSR for each paired calibration data point, and then averaging them together, either unweighted or weighted by temporal order of by elapsed time.

As discussed above, particular embodiments described herein utilize a least squares linear regression computation to calibrate the glucose monitor 100 and/or analyze sensor data using post-processor 200, for example. However, alternative embodiments may utilize a multiple component linear regression computation with more variables than just the paired calibration data points discussed above, to account for additional calibration effecting parameters, such as environment, an individual user's characteristics, sensor lifetime, manufacturing characteristics (such as lot characteristics), deoxidization, enzyme concentration fluctuation and/or degradation, power supply variations, and/or the like.

In particular implementations, after a first calibration is performed on a particular glucose sensor 12, subsequent calibrations may employ a weighted average using a sensitivity ratio (SPSR, MSPSR, LRSR, or MLRSR) calculated from data collected since the last calibration, and previous sensitivity ratios calculated for previous calibrations. Here, an initial sensitivity ratio (SR1) may be calculated immediately after initialization/stabilization using a paired calibration data point, and used by glucose monitor 100 or post processor 200 until a second sensitivity ratio (SR2) is calculated. Here, second sensitivity ratio SR2 may comprise an average of SR1 and the sensitivity ratio as calculated using the paired calibration data points since the initial calibration (SRday1) as follows:

$$SR2 = \frac{SR1 + SRday1}{2}$$

The third sensitivity ratio (SR3) is an average of SR2 and the sensitivity ratio as calculated using the paired calibration data points since the second calibration (SRday2). The equation is as follows:

$$SR3 = \frac{SR2 + SRday2}{2}$$

Sensitivity ratios for successive days may be similarly determined as follows:

$$SR_n = \frac{SR_{(n-1)} + SRday_{(n-1)}}{2},$$

where:

$SR_n$ is the new sensitivity ratio calculated at the beginning of time period, n, using data from time period (n-1), to be used by glucose monitor 100, to convert Valid ISIGs measurement values to blood glucose readings throughout time period n;

$SR_{(n-1)}$ is a previous sensitivity ratio calculated at the beginning of time period n-1, using data from time period n-2; and $SRday_{(n-1)}$ is the sensitivity ratio calculated using paired calibration data points collected since the last calibration.

Alternatively, previous sensitivity ratios may be ignored and SR may be calculated using only the paired calibration data points since the last calibration. In another alternative, all previous SRs may be averaged with the latest SR calculated using only the paired calibration data points since the last calibration. In other implementations, the paired calibration data points are used to establish an equation for a curve representing SR over time. The curve may then used to extrapolate SR to be used until the next paired calibration data point is entered.

In embodiments that use a post processor 200 to evaluate a sensitivity ratio, such a sensitivity ratio may be calculated using paired calibration data points over a period of time since a last calibration, and is not averaged with previous sensitivity ratios. A sensitivity ratio determined for a period of time may then be applied to the same period of time over which the paired calibration data points were collected. This may result in a more accurate than the real-time case described above for the glucose monitor 100 because, in the real-time case, sensitivity ratios from a previous time period must be used to calculate the blood glucose level in the present time period. If the sensitivity ratio has changed over time, estimation of blood glucose using an old sensitivity ratio may introduce an error.

In particular embodiments, once calibration is complete, Valid ISIG values may be converted to blood glucose readings based on a particular version of the sensitivity ratio, and the resulting blood glucose readings are compared to an out-of-range limit. If such a resulting calculated blood glucose level is greater than a maximum out-of-range limit of 200 mg/dl (or equivalently 3600 mmol/l), the out-of-range alarm is activated. This is a calibration cancellation event, therefore, ISIG values are no longer valid once this alarm is activated. Blood glucose readings are either not calculated, or at least not considered reliable, until the glucose monitor 100 or post processor 200 is re-calibrated. The user may be notified of the alarm and that re-calibration is needed.

In alternative embodiments, higher or lower maximum out-of-range limits may be used depending on the sensor characteristics, the characteristic being measured, the user's body characteristics, and the like. In particular implementations, a minimum out-of-range limit may be used or both a maximum and a minimum out-of-range limits may be used. In other particular embodiments, such out-of-range limits may not cause blood glucose readings to become invalid and/or re-calibration is not required; however, an alarm could still be provided. In additional particular embodiments, an alarm may be activated in response to two or more ISIG values exceeding an out-of-range limit. ISIG values that are out-of-range may be omitted from display.

In alternative embodiments, calibration may be conducted by injecting a fluid containing a known value of glucose into the site around the glucose sensor set 10, followed by sending one or more glucose sensor readings to glucose monitor 100. The readings may then be processed (filtered, smoothed, clipped, averaged, and/or the like) and used along with the known glucose value to calculate the SR for the glucose sensor 12. Particular alternative embodiments may use a glucose sensor set of the type described in U.S. Pat. No. 5,951,521 entitled "A Subcutaneous Implantable Sensor Set Having the Capability To Remove Or Deliver Fluids To An Insertion Site".

In other alternative embodiments, glucose sensor 12 may be supplied with a vessel containing a solution with a known glucose concentration to be used as a reference, and glucose sensor 12 is immersed into the reference glucose solution during calibration. Glucose sensor 12 may be shipped in the reference glucose solution, for example. As described above, glucose sensor readings may be used to calculate a sensitivity ratio given a known (or independently measured) glucose concentration of the solution.

In another alternative embodiment, glucose sensors 12 may be calibrated during a manufacturing process. Sensors from the same manufacturing lot have similar properties may be calibrated using a sampling of glucose sensors 12 from the population and a solution with a known glucose concentration. A sensitivity ratio is provided with the glucose sensor 12 and is entered into glucose monitor 100 or post processor 200 by the user or another individual.

In addition, although the particular process of FIG. 18 includes specific operations occurring in a particular order, in alternative embodiments, certain of these operations may be performed in a different order, modified, or removed while not deviating from claimed subject matter. Moreover, other operations may be added to and/or combined with the above described process without deviating from claimed subject matter. For example, although in the particular embodiment of FIG. 16 the variable Recal is never reset to no fail, potentially, an additional operation may be added to reset Recal to no fail if no cal error alarms are triggered after a predetermined number of calibrations.

Unless specifically stated otherwise, as apparent from the following discussion, it is appreciated that throughout this specification discussions utilizing terms such as "processing", "computing", "calculating", "determining", "estimating", "selecting", "weighting", "identifying", "obtaining", "representing", "receiving", "transmitting", "storing", "analyzing", "creating", "contracting", "associating", "updating", or the like refer to the actions or processes that may be performed by a computing platform, such as a computer or a similar electronic computing device, that manipulates or transforms data represented as physical, electronic or magnetic quantities or other physical quantities within the computing platform's processors, memories, registers, or other information storage, transmission, reception or display devices. Accordingly, a computing platform refers to a system or a device that includes the ability to process or store data in the form of signals. Thus, a computing platform, in this context, may comprise hardware, software, firmware or any combinations thereof. Further, unless specifically stated otherwise, a process as described herein, with reference to flow diagrams or otherwise, may also be executed or controlled, in whole or in part, by a computing platform.

It should be noted that, although aspects of the above system, method, or process have been described in a particular order, the specific order is merely an example of a process and claimed subject matter is of course not limited to the order described. It should also be noted that the systems, methods, and processes described herein, may be capable of being performed by one or more computing platforms. In addition, the methods or processes described herein may be capable of being stored on a storage medium as one or more machine readable instructions, that if executed may enable a computing platform to perform one or more actions. "Storage medium" as referred to herein relates to media capable of storing information or instructions which may be operated on, or executed by, by one or more machines. For example, a storage medium may comprise one or more storage devices for storing machine-readable instructions or information. Such storage devices may comprise any one of several media types including, for example, magnetic, optical or semiconductor storage media. For further example, one or more computing platforms may be adapted to perform one or more of the processed or methods in accordance with claimed subject matter, such as the methods or processes described herein. However, these are merely examples relating to a storage medium and a computing platform and claimed subject matter is not limited in these respects.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

What is claimed is:

1. A method comprising:
    obtaining samples of an electrical signal generated by a sensor, said samples having sample values responsive to a blood-glucose concentration in a patient;
    obtaining blood glucose reference measurement values responsive to said blood-glucose concentration;
    pairing at least some of the sample values with temporally associated blood glucose reference measurement values;
    for at least one of said paired sample values, weighting said paired sample value based, at least in part, on a measure of statistical dispersion of said electrical signal, said measure of statistical dispersion of said electrical signal being a function of a blood glucose reference measurement value paired with said sample value;
    determining one or more parameters of an estimator of said blood-glucose concentration based, at least in part, on said weighted paired sample values; and
    controlling a pump to infuse a substance to said patient based, at least in part, on said determined one or more parameters of said estimator of said blood-glucose concentration.

2. The method of claim 1, wherein said determining said one or more parameters comprises determining said one or more parameters based, at least in part, on a linear regression of said weighted paired sample values and temporally associated blood-glucose reference measurement values.

3. The method of claim 2, wherein said determining said one or more parameters of said estimator further comprises:
    calculating a linear regression sensitivity ratio based, at least in part, on said weighted paired sample values and temporally associated blood-glucose reference measurement values;
    selecting an offset based, at least in part, on said calculated linear regression sensitivity ratio; and
    calculating a modified linear regression sensitivity ratio based, at least in part, on said selected offset, said weighted paired sample values and said associated blood-glucose reference measurement values.

4. The method of claim 1, wherein said measure of statistical dispersion comprise a variance and/or approximation of a variance of said paired sample values as a function of said temporally associated blood glucose reference measurement values.

5. The method of claim 1, wherein said at least some of said paired sample values are weighted according to an inverse of said measure of statistical dispersion of said paired sample values.

6. The method of claim 1, and further comprising:
    estimating a linear relationship of said measure of statistical dispersion of said electrical signal versus blood glucose concentration; and
    deriving said one or more parameters based, at least in part, on said linear relationship.

7. The method of claim 1, wherein individually weighting said at least some of said paired sample values further comprises further weighting said paired sample values based on how recently said ample values are obtained.

8. The method of claim 1, and further comprising detecting a failure of said sensor based, at least in part, on a change in said determined one or more parameters.

9. The method of claim 1, and further comprising calibrating measurements from said sensor for measuring a blood-glucose concentration based, at least in part, on said determined one or more parameters.

10. The method of claim 1, wherein said individually weighting said at least some of said paired sample values comprises weighting said at least some of said paired sample values according to a decreasing function of blood glucose reference measurement values temporally associated with said weighted paired sample values.

11. An article comprising:
    a non-transitory storage medium comprising machine-readable instructions stored thereon which are executable by a computing platform to:
    obtain samples of an electrical signal generated by a sensor, said samples having sample values responsive to a blood-glucose concentration in a patient;
    obtain blood glucose reference measurement values indicative of said blood-glucose concentration;
    pair at least some of said sample values with temporally associated blood glucose reference measurement values;
    for at least one of said paired sample values, weighting said paired sample value based, at least in part, on a measure of statistical dispersion of said electrical signal, said measure of statistical dispersion of said electrical signal being a function of a blood glucose reference sample value paired with said sample value;
    determining one or more parameters of an estimator of said blood-glucose concentration based, at least in part, on said weighted paired sample values; and
    control a pump to infuse a substance to said patient based, at least in part, on said determined one or more parameters of said estimator of said blood-glucose concentration.

12. The article of claim 11, wherein said instructions are further executable by said computing platform to determine said one or more parameters based, at least in part, on a linear regression of said weighted paired sample values and temporally associated blood-glucose reference measurement values.

13. The article of claim 12, wherein said instructions are further executable by said computing platform to:
    calculate a linear regression sensitivity ratio based, at least in part, on said weighted paired sample values and temporally associated blood-glucose reference measurement values;

select an offset based, at least in part, on said calculated linear regression sensitivity ratio; and calculate a modified linear regression sensitivity ratio based, at least in part, on said selected offset, said weighted paired sample values and said temporally associated blood-glucose reference measurement values.

14. The article of claim 11, wherein said measure of statistical dispersion comprises a variance and/or approximation of a variance of said sample values as a function of said temporally associated blood glucose reference measurement values.

15. The article of claim 11, wherein said at least some of said weighted paired sample values are weighted according to an inverse of said measure of statistical dispersion of said weighted paired sample values.

16. The article of claim 11, wherein said instructions are further executable by said computing platform to:

estimate a linear relationship of said measure of statistical dispersion of said electrical signal versus blood glucose concentration; and derive said function based, at least in part, on said linear relationship.

17. The article of claim 11, wherein instructions are further executable by said computing platform to individually weight said paired sample values based on how recently said sample values are obtained.

18. The article of claim 11, wherein said instructions are further executable by said computing platform to detect a failure of said sensor based, at least in part, on a change in said determined one or more parameters.

19. The article of claim 11, wherein said instructions are further executable by said computing platform to calibrate measurements from said sensor for measuring a blood-glucose concentration based, at least in part, on said determined one or more parameters.

20. The article of claim 11, wherein said instructions are further executable by said computing platform to individually weight said at least some of said paired sample values according to a decreasing function of blood glucose reference values temporally associated with said paired sample values.

21. An apparatus comprising:

a sensor to generate one or more sensor signals responsive to a blood glucose concentration in a body;

a computing platform to:

obtain samples of said one or more signals, said samples having sample values responsive to said blood-glucose concentration in a patient;

obtain blood glucose reference measurement values responsive to said blood-glucose concentration;

for at least one of said paired sample values, weighting said paired sample value based, at least in part, on a measure of statistical dispersion of said electrical signal, said measure of statistical dispersion of said one or more sensor signals being a function of a blood glucose reference sample value paired with said sample value;

determine one or more parameters of an estimator of said blood-glucose concentration based, at least in part, on said weighted paired sample values; and control a pump to infuse a substance to said patient based, at least in part, on said determined one or more parameters of said estimator of said blood-glucose concentration.

22. The apparatus of claim 21, wherein said computing platform is further to determine said one or more parameters based, at least in part, on a linear regression of said weighted paired sample values and temporally associated blood-glucose reference measurement values.

23. The apparatus of claim 22, wherein said computing platform is further to:

calculate a linear regression sensitivity ratio based, at least in part, on said weighted paired sample values and temporally associated blood-glucose reference measurement values;

select an offset based, at least in part, on said calculated linear regression sensitivity ratio; and calculate a modified linear regression sensitivity ratio based, at least in part, on said selected offset, said weighted paired sample values and said temporally associated blood-glucose reference measurement values.

24. The apparatus of claim 21, wherein said measure of statistical dispersion comprises a variance and/or approximation of a variance of said sample values as a function of said temporally associated blood glucose reference measurement values.

25. The apparatus of claim 21, wherein said paired sample values are weighted according to an inverse of said measure of statistical dispersion of said one or more sensor signals.

26. The apparatus of claim 21, wherein said computing platform is further to:

estimate a linear relationship of said measure of statistical dispersion of said one or more sensor signals versus blood glucose concentration; and derive said one or more parameters based, at least in part, on said linear relationship.

27. The apparatus of claim 21, wherein said computing platform is further to further weight said paired sample values based on how recently said paired sample values are obtained from said sensor.

28. The apparatus of claim 21, wherein said computing platform is further to detect a failure of said sensor based, at least in part, on a change in said estimated one or more parameters.

29. The apparatus of claim 21, wherein said computing platform is further to calibrate measurements from said sensor for measuring a blood-glucose concentration based, at least in part, on said estimated one or more parameters.

30. The apparatus of claim 21, wherein said computing platform is further to individually weight said at least some of said sample values by weighting said at least some of said sample values according to a decreasing function of blood glucose reference measurement values temporally associated with said weighted sample values.

* * * * *